(12) United States Patent
Bergmann

(10) Patent No.: US 10,605,812 B2
(45) Date of Patent: Mar. 31, 2020

(54) METHOD FOR PREDICTING THE RISK OF GETTING CANCER OR DIAGNOSING CANCER IN A SUBJECT

(71) Applicant: SphingoTec GmbH, Hennigsdorf (DE)

(72) Inventor: Andreas Bergmann, Berlin (DE)

(73) Assignee: SphingoTec GmbH, Hennigsdorf (DE)

( * ) Notice: Subject to any disclaimer, the term of this patent is extended or adjusted under 35 U.S.C. 154(b) by 767 days.

(21) Appl. No.: 14/759,724

(22) PCT Filed: Jan. 7, 2014

(86) PCT No.: PCT/EP2014/050144
§ 371 (c)(1),
(2) Date: Jul. 8, 2015

(87) PCT Pub. No.: WO2014/108397
PCT Pub. Date: Jul. 17, 2014

(65) Prior Publication Data
US 2015/0346207 A1     Dec. 3, 2015

(30) Foreign Application Priority Data
Jan. 8, 2013  (EP) .................................... 13150564

(51) Int. Cl.
| | | |
|---|---|---|
| *G01N 31/00* | (2006.01) | |
| *G01N 33/53* | (2006.01) | |
| *G01N 33/574* | (2006.01) | |
| *G01N 33/74* | (2006.01) | |

(52) U.S. Cl.
CPC . *G01N 33/57488* (2013.01); *G01N 33/57415* (2013.01); *G01N 33/57423* (2013.01); *G01N 33/74* (2013.01); *G01N 2333/62* (2013.01); *G01N 2333/70* (2013.01); *G01N 2410/00* (2013.01)

(58) Field of Classification Search
None
See application file for complete search history.

(56) References Cited

U.S. PATENT DOCUMENTS 5,268,359 A * 12/1993 Harmar .................... C07K 7/22
514/18.1
7,838,245 B2 * 11/2010 Bergmann ............. G01N 33/68
435/336
9,188,591 B2 * 11/2015 Bergmann ............. G01N 33/68
9,702,876 B2 * 7/2017 Bergmann ....... G01N 33/57415
2008/0260640 A1 * 10/2008 Bergmann ............. G01N 33/68
424/9.1
2011/0275091 A1 * 11/2011 Bergmann ............. G01N 33/68
435/7.1

FOREIGN PATENT DOCUMENTS

| DE | 102005003687 A1 * | 7/2006 | ............. G01N 33/74 |
|---|---|---|---|
| WO | 2005/103712 A2 | 11/2005 | |
| WO | WO-2005103712 A2 * | 11/2005 | ............. G01N 33/68 |

OTHER PUBLICATIONS

Tascilar et al. (Annals of Oncology 10,Suppl. 4:S107-S110, 1999).*
Tockman et al. (Cancer Research 52:2711s-2718s, 1992).*
International Search Report dated Jun. 17, 2014 issued in corresponding PCT/EP2014/050144 application (pp. 1-6).
Written Opinion issued in corresponding PCT/EP2014/050144 application (pp. 1-8).
J.M. Nesland et al., "C-erbB-2 Protein and Neuroendocrine Expression in Breast Carcinomas", Anticancer Research, vol. 11, No. 1 (1991) pp. 161-167.
J. Alumets et al., "Neurohormonal Peptides in Endocrine Tumors of the Pancreas, Stomach, and Upper Small Intestine: I. An Immunohistochemical Study of 27 Cases", Ultrastructural Pathology, vol. 5, No. 1 (1983) pp. 55-72.
I.U. Khan et al., "Targeted Tumor Diagnosis and Therapy with Peptide Hormones as Radiopharmaceuticals", Anti-Cancer Agents in Medicinal Chemistry, vol. 8, No. 2 (2008) pp. 186-199.
B.Y. Reddy et al., "Neurokinin Receptors as Potential Targets in Breast Cancer Treatment", Current Drug Discovery Technologies, vol. 5, No. 1 (2008) pp. 15-19.
J.E.S. Ardill et al., "The Importance of the Measurement of Circulating Markers in Patients with Neuroendocrine Tumours of the Pancreas and Gut", Endocrine-Related Cancer, vol. 10, No. 4 (2003) pp. 459-462.
G.B. Turner et al., "Circulating Markers of Prognosis and Response to Treatment in Patients with Midgut Carcinoid Tumours", Gut, vol. 55, No. 11 (2006) pp. 1586-1591.

* cited by examiner

*Primary Examiner* — Lisa V Cook
(74) *Attorney, Agent, or Firm* — Millen White Zelano and Branigan, PC; John Sopp

(57) ABSTRACT

A method for predicting the risk of getting cancer in a subject that does not suffer from cancer or alternatively diagnosing cancer in a subject, where the method includes determining the level of Pro-Tachykinin, its splice variants or fragments thereof of at least 5 amino acids, where the fragments including Substance P and Neurokinin, in a bodily fluid obtained from the subject; and correlating the level of Pro-Tachykinin, its splice variants or fragments thereof with a risk for getting cancer, wherein a reduced Pro-Tachykinin level is predictive for an enhanced risk of getting cancer or alternatively diagnosing cancer wherein a reduced level is correlated with the diagnosis of cancer.

Figure 1:
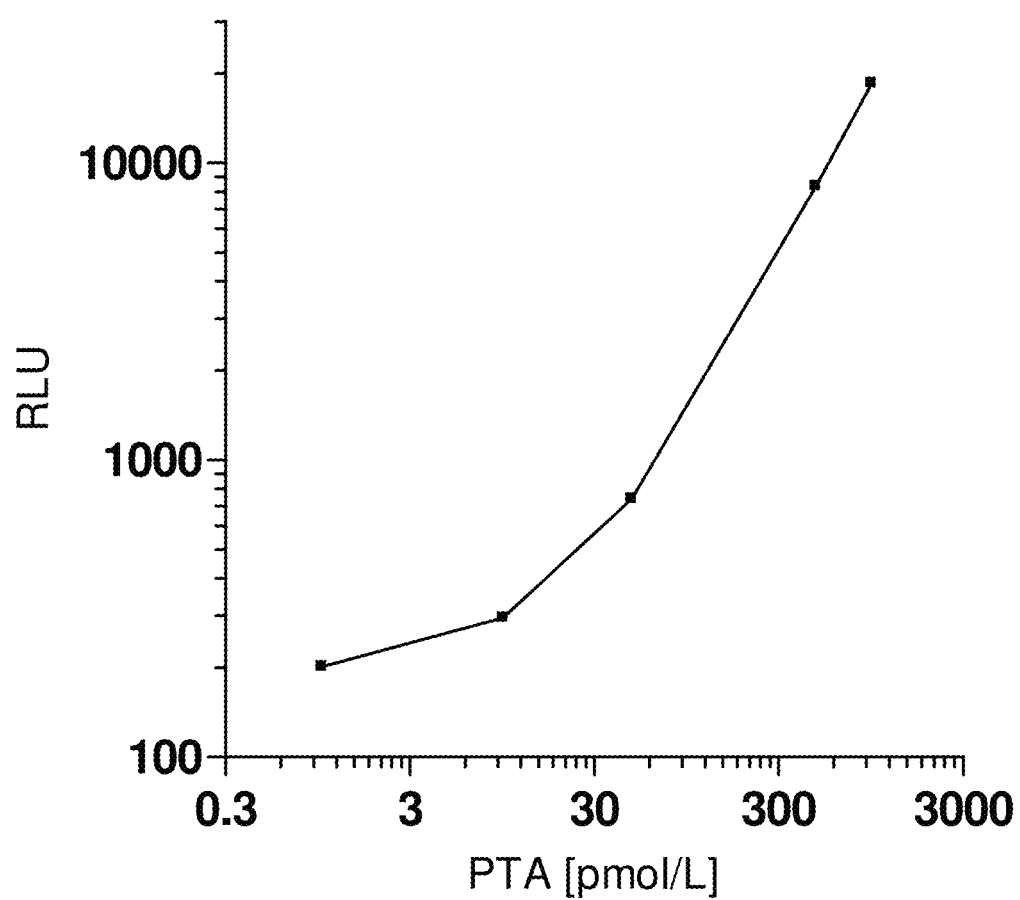

27 Claims, 5 Drawing Sheets
Specification includes a Sequence Listing.

METHOD FOR PREDICTING THE RISK OF GETTING CANCER OR DIAGNOSING CANCER IN A SUBJECT

Subject matter of the present invention is a method for predicting the risk of getting cancer in a subject that does not suffer from cancer or alternatively diagnosing cancer in a subject comprising:

determining the level of Pro-Tachykinin or fragments thereof of at least 5 amino acids including Substance P and Neurokinin in a bodily fluid obtained from said subject; and correlating said level of Pro-Tachykinin or fragments thereof with a risk for getting cancer, wherein a reduced level is predictive for an enhanced risk of getting cancer or alternatively diagnosing cancer wherein an reduced level is correlated with the diagnosis of cancer.

Substance P (SP) is a neuropeptide: an undecapeptide that functions as a neurotransmitter and as a neuromodulator. It belongs to the tachykinin neuropeptide family. Substance P and its closely related neuropeptide neurokinin A (NKA) are produced from a polyprotein precursor after differential splicing of the prePro-Tachykinin A gene. In the CNS, Substance P participates in the pain transmission system.

Substance P plays roles in inflammatory processes (Ang et al., 2011) and possesses antiapoptotic activitiy in cancer cells (Munoz et al., 2005).

The Substance P receptor (Neurokinin1 receptor) plays a crucial role in the development of cancer (Fries et al., 2003; Munoz et al., 2010; Rameshwar, 2007; Schulz et al., 2006). Blocking the Substance P pathway markedly reduced tumor cell growth in vitro (for review see Munoz and Rossow, 2009).

The use of vasoactive peptides for prediction of cancer risks in males has been reported by Belting et al., Cancer, Epidemiology, Biomarkes & Prevention. MR-pro-ANP, MR-pro-ADM and copeptin was measured in the fasting plasma from participants of the Malmö Diet and Cancer Study that were free from cancer prior to the baseline exam in 1991 to 1994 (1768 males and 2293 females). The authors stated that among females, there was no relationship between biomarkers and cancer incidence.

A subject of the present invention was to investigate the prognostic and diagnostic power of Pro-Tachykinin for the prediction of cancer incidence and the prediction of the risk of reoccurrence of cancer. To address this issue, stable fragments of Pro-Tachykinin (Ernst et al., 2008) in fasting plasma were measured in said Swedish prospective cohort study (Malmö Diet and Cancer Study) and related baseline level of this biomarker to breast-cancer incidence during 15 years of follow-up.

Surprisingly, it has been shown that Pro-Tachykinin is a powerful and highly significant biomarker for predicting the risk of getting cancer in a subject that does not suffer from cancer or alternatively diagnosing cancer in a subject.

Thus, subject matter of the present invention is a method for predicting the risk of getting cancer in a subject that does not suffer from cancer or alternatively diagnosing cancer in a subject comprising:

determining the level of Pro-Tachykinin, its splice variants or fragments thereof of at least 5 amino acids including Substance P and Neurokinin in a bodily fluid obtained from said subject; and correlating said level of Pro-Tachykinin, its splice variants or fragments thereof with a risk for getting cancer, wherein an reduced level is predictive for an enhanced risk of getting cancer or alternatively diagnosing cancer wherein an reduced level is correlated with the diagnosis of cancer.

In another subject of the invention said method additionally comprises the following steps: determining additionally the level of Pro-Neurotensin or fragments thereof of at least 5 amino acids in a bodily fluid obtained from said subject; and correlating additionally said level of Pro-Neurotensin or fragments thereof of at least 5 amino acids with a risk for getting cancer, wherein an increased level of Pro-Neurotensin or fragments thereof is predictive for an enhanced risk of getting cancer or alternatively diagnosing cancer wherein an increased level of Pro-Neurotensin or fragments thereof is correlated with the diagnosis of cancer.

According to another embodiment of the invention the above methods may additionally comprise the following steps:

determining additionally the level of Pro-Enkephalin or fragments thereof of at least 5 amino acids in a bodily fluid obtained from said subject; and correlating additionally Pro-Enkephalin or fragments thereof of at least 5 amino acids with a risk for getting cancer, wherein an reduced level of Pro-Enkephalin or fragments thereof is predictive for an enhanced risk of getting cancer or alternatively diagnosing cancer wherein an reduced level of Pro-Enkephalin or fragments thereof is correlated with the diagnosis of cancer.

According to another embodiment of the invention the above methods may additionally comprise the following steps:

determining additionally the level of Insulin in a bodily fluid obtained from said subject; and correlating additionally said level of Insulin with a risk for getting cancer, wherein an reduced level of Insulin is predictive for an enhanced risk of getting cancer or alternatively diagnosing cancer wherein an reduced level is correlated with the diagnosis of cancer.

Thus, the methods according to the present invention comprise the determination of the level of Pro-Tachykinin, its splice variants or fragments thereof of at least 5 amino acids including Substance P and Neurokinin, in a bodily fluid and may optionally further comprise at least one further determination and additional correlation with the risk of cancer selected from the group comprising:

determination of the level of Pro-Neurotensin or fragments thereof at least 5 amino acids and determination of the level of Pro-Enkephalin or fragments thereof of at least 5 amino acids and determination of the level of Insulin.

In one embodiment of the invention at least one of the before mentioned additional biomarkers is further determined and additionally correlated with said cancer risk in addition to Pro-Tachykinin, its splice variants or fragments thereof of at least 5 amino acids including Substance P and Neurokinin. In one embodiment of the invention at least two of the before mentioned additional biomarkers are further determined and additionally correlated with said risk in addition to Pro-Tachykinin, its splice variants or fragments thereof of at least 5 amino acids including Substance P and Neurokinin. In one embodiment all of the above four biomarkers are determined.

In one specific embodiment of the above methods wherein in addition to Pro-Tachykinin, its splice variants or fragments thereof of at least 5 amino acids including Substance P and Neurokinin further biomarker are determined and correlated with said risk "additionally correlating" means a combined analysis of the determined biomarker levels by taking into account the relative risk factors for cancer development obtained by the individual biomarkers.

The combined analysis of more than one marker is as an example explained in Example 5. The person skilled in the art knows statistical methods that may perform combined analysis of more than one marker or parameter.

In one embodiment of the above methods a reduced level of Pro-Tachykinin, its splice variants or fragments thereof is a level below a threshold wherein said threshold is about or below 100 pmol/l, preferably about or below 80 pmol/L, preferably about or below 60 pmol/L, preferably about or below 50 pmol/L, preferably about or below 45.6 pmol/L, preferably about 40 pmol/L In one embodiment of the above methods an increased level of Pro-Neurotensin or fragments thereof is a level above a threshold wherein said threshold is about or above 78 pmol/l PNT, preferred about or above 100 pmol/l, more preferred about 150 pmol/l.

In one embodiment of the above methods a reduced level of Pro-Enkephalin or fragments thereof is a level below a threshold wherein said threshold is about or below 100 pmol/l, preferably about or below 75 pmol/L, preferably about or below 50 pmol/L, preferably about 40.4 pmol/L.

In one embodiment of the above methods a reduced level of Insulin is a level below a threshold wherein said threshold is about 70 pmol/l.

Thresholds have to be seen in light of the calibration method used and the above values have to be seen in light of the assays and calibration methods used in the present examples 1, 3 and 4.

In one special embodiment said subject is female. In one special embodiment said subject is female and said cancer is breast cancer.

In one special embodiment said cancer is lung cancer.

Further examples of cancers may be selected from the group comprising breast cancer, lung cancer, pancreatic cancer and colon cancer.

Throughout the specification the term Pro-Tachykinin and Pro-Tachykinin A (PTA) are used synonymously. The term includes all splice variants of Pro-Tachykinin A, namely αPTA, βPTA, γPTA, and δPTA. Throughout the specification it should be understood that the term fragments of Pro-Tachykinin also include Substance P and Neurokinin.

The term "determining the level of Pro-Tachykinin, its splice variants or fragments thereof of at least 5 amino acids including Substance P and Neurokinin" means that usually the immunoreactivity towards a region within the before mentioned molecules is determined. This means that it is not necessary that a certain fragment is measured selectively. It is understood that a binder which is used for the determination of the level of Pro-Tachykinin or fragments thereof of at least 5 amino acids including Substance P and Neurokinin binds to any fragment that comprises the region of binding of said binder. Said binder may be an antibody or antibody fragment or an non-IgG Scaffold.

Thus, subject matter of the present invention is in one embodiment the determination of the susceptibility of a male or woman to aquire cancer, e.g. breast cancer, lung cancer etc.

Data obtained in the Malmö study revealed a correlation between the risk of getting cancer in male subjects with the level of Pro-Tachykinin, its splice variants or fragments thereof of at least 5 amino acids in a bodily fluid obtained from said male subject; this correlation however, was not that statistically significant for the present data set although there was a clear trend for an increased cancer risk at reduced levels of Pro-Tachykinin, its splice variants or fragments thereof also in males. Thus, there is a value for the method according to the invention also for male subjects but in the present study the observed effect was not as strong for males as compared to females. This may be primarily due to the low number of cancer incidents in the male population.

The term "subject" as used herein refers to a living human or non-human organism. Preferably herein the subject is a human subject.

The term "reduced level" means a level below a certain threshold level. The term "increased level" means a level above a certain threshold. A bodily fluid may be selected from the group comprising blood, serum, plasma, urine, cerebrospinal liquid (csf), and saliva.

In a special embodiment said bodily fluid is blood, serum or plasma.

In one embodiment of the invention said subject has never had a diagnosed cancer at the time the sample of bodily fluid is taken from said subject.

In another embodiment said subject has been diagnosed before with having cancer and has been cured at the time the sample of bodily fluid is taken from said subject and the risk of reoccurrence of getting cancer is determined or alternatively the re-occurrence of cancer is predicted.

Pro-Tachykinin may have the following sequence(s):

```
(Pro-Tachykinin A (1-107)
                                         SEQ ID NO. 1
EEIGANDDLNYWSDWYDSDQIKEELPEPFEHLLQRIARRPKPQQFFGLMG

KRDADSSIEKQVALLKALYGHGQISHKRHKTDSFVGLMGKRALNSVAYER

SAMQNYERRR
```

Fragments of Pro-Tachykinin that may be determined in a bodily fluid may be e.g. selected from the group of the following fragments:

```
(Pro-Tachykinin 1-37, P37)
                                         SEQ ID NO. 2
EEIGANDDLNYWSDWYDSDQIKEELPEPFEHLLQRIA (Substance P)
                                         SEQ ID NO. 3
RPKPQQFFGLM(-NH2)

(Neuropeptide K)
                                         SEQ ID NO. 4
DADSSIEKQVALLKALYGHGQISHKRHKTDSFVGLM(-NH2)

(Neuropeptide Gamma)
                                         SEQ ID NO. 5
GHGQISHKRHKTDSFVGLM(-NH2)

(Neurokinin 1)
                                         SEQ ID NO. 6
HKTDSFVGLM(-NH2)

(C-terminal flanking peptide, PTA 1 92-107)
                                         SEQ ID NO. 7
ALNSVAYERSAMQNYE (PTA Isoform alpha)
                                         SEQ ID NO. 8
EEIGANDDLNYWSDWYDSDQIKEELPEPFEHLLQRIARRPKPQQFFGLMG

KRDADSSIEKQVALLKALYGHGQISHKMAYERSAMQNYERRR
```

-continued (PTA Isoform beta)
SEQ ID NO. 9
EEIGANDDLNYWSDWYDSDQIKEELPEPFEHLLQRIARRPKPQQFFGLMG

KRDADSSIEKQVALLKALYGHGQISHKRHKTDSFVGLMGKRALNSVAYER

SAMQNYERRR (PTA Isoform delta)
SEQ ID NO. 10
EEIGANDDLNYWSDWYDSDQIKEELPEPFEHLLQRIARRPKPQQFFGLMG

KRDAGHGQISHKMAYERSAMQNYERRR (PTA Isoform gamma)
SEQ ID NO. 11
EEIGANDDLNYWSDWYDSDQIKEELPEPFEHLLQRIARRPKPQQFFGLMG

KRDAGHGQISHKRHKTDSFVGLMGKRALNSVAYERSAMQNYERRRSEQ (PTA3-22)
SEQ ID NO. 12
GANDDLNYWSDWYDSDQIK (PTA 21-36)
SEQ ID NO. 13
IKEELPEPFEHLLQRI

Determining the level of PTA, its splice variants or fragments thereof may mean that the immunoreactivity towards PTA or fragments thereof including Substance P and Neurokinin is determined. A binder used for determination of PTA, its splice variants or fragments thereof depending of the region of binding may bind to more than one of the above displayed molecules. This is clear to a person skilled in the art.

In a more specific embodiment of the method according to the present invention the level of P37 (PTA 1-37, SEQ ID NO. 2, EEIGANDDLNYWSDWYDSDQIKEELPEPFE-HLLQRIA) is determined. In an even more specific embodiment according to the present invention at least one or two binders are used that bind to PTA 1-37, SEQ ID NO. 2, EEIGANDDLNYWSDWYDSDQIKEELPEPFE-HLLQRIA, in case of more than one binder they bind preferably to two different regions within PTA 1-37, SEQ ID NO. 2, EEIGANDDLNYWSDWYDSDQIKEELPEPFE-HLLQRIA. Said binder(s) may preferably be an antibody or a binding fragment thereof.

In an even more specific embodiment binder(s) are used for the determination of PTA its variants and fragments that bind to one or both, respectively, of the following regions within PTA 1-37:

PTA 3-22
(SEQ ID NO. 12)
GANDDLNYWSDWYDSDQIK

PTA 21-36
(SEQ ID NO. 13)
IKEELPEPFEHLLQRI

In a specific embodiment the level of PTA, its splice variants or fragments thereof are measured with an immunoassay using antibodies or fragments of antibodies binding to PTA, its splice variants or fragments thereof. An immunoassay that may be useful for determining the level of PTA, its splice variants or fragments thereof of at least 5 amino acids may comprise the steps as outlined in Example 1. All thresholds and values have to be seen in correlation to the test and the calibration used according to Example 1. A person skilled in the art may know that the absolute value of a threshold might be influenced by the calibration used. This means that all values and thresholds given herein are to be understood in context of the calibration used in herein (Example 1).

According to the invention the diagnostic binder to PTA or the other additional biomarkers is selected from the group consisting of antibodies e.g. IgG, a typical full-length immunoglobulin, or antibody fragments containing at least the F-variable domain of heavy and/or light chain as e.g. chemically coupled antibodies (fragment antigen binding) including but not limited to Fab-fragments including Fab minibodies, single chain Fab antibody, monovalent Fab antibody with epitope tags, e.g. Fab-V5Sx2; bivalent Fab (miniantibody) dimerized with the CH3 domain; bivalent Fab or multivalent Fab, e.g. formed via multimerization with the aid of a heterologous domain, e.g. via dimerization of dHLX domains, e.g. Fab-dHLX-FSx2; F(ab')2-fragments, scFv-fragments, multimerized multivalent or/and multispecific scFv-fragments, bivalent and/or bispecific diabodies, BITE® (bispecific T-cell engager), trifunctional antibodies, polyvalent antibodies, e.g. from a different class than G; single-domain antibodies, e.g. nanobodies derived from camelid or fish immunoglobulines.

In a specific embodiment the level of PTA, its splice variants or fragments thereof or the other additional biomarkers is measured with an assay using binders selected from the group comprising aptamers, non-Ig scaffolds as described in greater detail below binding to PTA, its splice variants or fragments thereof or alternatively to the additional biomarkers.

Binder that may be used for determining the level of PTA, its splice variants or fragments thereof exhibit an affinity constant to PTA, its splice variants or fragments thereof of at least $10^7$ $M^{-1}$, preferred $10^8$ $M^{-1}$, preferred affinity constant is greater than $10^9$ $M^{-1}$, most preferred greater than $10^{10}$ $M^{-1}$, A person skilled in the art knows that it may be considered to compensate lower affinity by applying a higher dose of compounds and this measure would not lead out-of-the-scope of the invention. Binding affinity may be determined using the Biacore method, offered as service analysis e.g. at Biaffin, Kassel, Germany.

Affinty Constants

To determine the affinity of the antibodies, the kinetics of binding of PTA, its splice variants or fragments thereof to immobilized antibody was determined by means of label-free surface plasmon resonance using a Biacore 2000 system (GE Healthcare Europe GmbH, Freiburg, Germany). Reversible immobilization of the antibodies was performed using an anti-mouse Fc antibody covalently coupled in high density to a CM5 sensor surface according to the manufacturer's instructions (mouse antibody capture kit; GE Healthcare). (Lorenz et al., "Functional Antibodies Targeting IsaA of *Staphylococcus aureus* Augment Host Immune Response and Open New Perspectives for Antibacterial Therapy"; Antimicrob Agents Chemother. 2011 January; 55(1): 165-173.)

A human PTA-control sample is available by ICI-Diagnostics, Berlin, Germany. The assay may also be calibrated by synthetic (for our experiments we used synthetic P37, SEQ ID NO. 2) or recombinant PTA, its splice variants or fragments thereof.

The threshold of PTA, its splice variants or fragments thereof for determining the risk of getting breast cancer in a female subject or diagnosing breast cancer in a female subject according to the methods of the present invention is below 100 pmol/l, preferably below 80 pmol/L, preferably below 60 pmol/L, preferably below 50 pmol/L, preferably below 45.6 pmol/L, preferably below 40 pmol/L. These thresholds are related to the above mentioned calibration method. A PTA value below said threshold means that the subject has an enhanced risk of getting cancer or has already cancer.

In one embodiment of the invention said method is performed more than once in order to monitor the risk of getting breast cancer in a female subject or in order to monitor the course of treatment. In one specific embodiment said monitoring is performed in order to evaluate the response of said female subject to preventive and/or therapeutic measures taken.

In one embodiment of the invention the method is used in order to stratify said subjects into risk groups.

Subject matter of the invention is further an assay for determining PTA, its splice variants or fragments in a sample comprising two binders that bind to two different regions within the region of PTA that is aminoacid 3-22 (GANDDLNYWSDWYDSDQIK, SEQ ID NO. 12) and aminoacid 21-36 (IKEELPEPFEHLLQRI, SEQ ID NO. 13) wherein each of said regions comprises at least 4 or 5 amino acids.

In one embodiment of the assays for determining PTA, its splice variants or fragments in a sample according to the present invention the analytical assay sensitivity of said assay is able to quantify the PTA, its splice variants or PTA fragments of healthy subjects and is <20 pmol/, preferably <10 pmol/l and more preferably <5 pmol/l.

In one embodiment of the assays for determining PTA, its splice variants or fragments in a sample according to the present invention such assay is a sandwich assay, preferably a fully automated assay. It may be an ELISA, a fully automated assay or a manual assay. It may be a so-called POC-test (point-of-care). Examples of automated or fully automated assay comprise assays that may be used for one of the following systems: Roche Elecsys®, Abbott Architect®, Siemens Centauer®, Brahms Kryptor®, Biomerieux Vidas®, Alere Triage®. Examples of test formats are provided above.

In one embodiment of the assays for determining PTA, its splice variants or fragments in a sample according to the present invention at least one of said two binders is labelled in order to be detected. Examples of labels are provided above.

In one embodiment of the assays for determining PTA, its splice variants or fragments in a sample according to the present invention at least one of said two binders is bound to a solid phase. Examples of solid phases are magnetic beads, polystyrene tubes or microtiterplates. In one embodiment a homogenous assay is used, i.e. using Time Resolved Amplified Cryptate Emission (TRACE) technologies.

In one embodiment of the assays for determining PTA, its splice variants or fragments in a sample according to the present invention said label is selected from the group comprising chemiluminescent label, enzyme label, fluorescence label, radioiodine label.

A further subject of the present invention is a kit comprising an assay according to the present invention wherein the components of said assay may be comprised in one or more container.

Subject of the present invention is also a method for predicting the risk of getting cancer in a female or identifying a subject having an enhanced risk for getting cancer according to any of the preceding embodiments, wherein the level of PTA, its splice variants or fragments thereof of at least 5 amino acids in a bodily fluid obtained from said subject either alone or in conjunction with other predictive laboratory or clinical parameters is used for the prediction of a subject's risk for getting an adverse event by a method which may be selected from the following alternatives:

Comparison with the median of the level of PTA, its splice variants or fragments thereof of at least 5 amino acids in a bodily fluid obtained from said subject in an ensemble of pre-determined samples in a population of "healthy" or "apparently healthy" subjects, Comparison with a quantile of the level of PTA, its splice variants or fragments thereof of at least 5 amino acids in a bodily fluid obtained from said subject in an ensemble of pre-determined samples in a population of "healthy" or "apparently healthy" subjects, Calculation based on Cox Proportional Hazards analysis or by using Risk index calculations such as the NRI (Net Reclassification Index) or the IDI (Integrated Discrimination Index).

In one embodiment of the invention subject of the present invention is also a method for predicting the risk of getting cancer in a female or identifying a subject having an enhanced risk for getting cancer according to any of the preceding embodiments, wherein the level of PTA, its splice variants or fragments thereof of at least 5 amino acids in a bodily fluid obtained from said subject either alone or in conjunction with other predictive biomarkers.

Such a useful additional biomarker may be Pro-Neurotensin and fragments thereof of at least 5 amino acids or Pro-Enkephalin and fragments thereof of at least 5 amino acids or Insulin.

In one specific embodiment of the method according to the present invention the level of Pro-Neurotensin 1-117 or fragments thereof is determined in addition to the determination of PTA, its splice variants or fragments thereof.

When it is referred to fragments throughout the present application said fragments comprise at least four or five amino acids.

Thus, subject matter of the present invention is also a method for predicting the risk of getting cancer in a subject that does not suffer from cancer or alternatively diagnosing cancer in a subject comprising:

determining the level of PTA, its splice variants or fragments thereof of at least 5 amino acids including Substance P and Neurokinin in a bodily fluid obtained from said subject; and determining the level of Pro-Neurotensin or fragments thereof of at least 5 amino acids in a bodily fluid obtained from said subject; and correlating said level of PTA, its splice variants or fragments thereof and Pro-Neurotensin or fragments thereof of at least 5 amino acids with a risk for getting cancer, wherein an reduced level of PTA, its splice variants or fragments thereof is predictive for an enhanced risk of getting cancer or alternatively diagnosing cancer wherein an reduced level of PTA, its splice variants or fragments thereof is correlated with the diagnosis of cancer and wherein an increased level of Pro-Neurotensin and fragments thereof is predictive for an enhanced risk of getting cancer or alternatively diagnosing cancer wherein an increased level of Pro-Neurotensin and fragments thereof is correlated with the diagnosis of cancer.

Pro-Neurotensin and fragments may have has the following sequence:

```
(Pro-Neurotensin 1-147)
                                            SEQ ID NO. 14
SDSEEEMKAL EADFLTNMHT SKISKAHVPS WKMTLLNVCS

LVNNLNSPAE ETGEVHEEEL VARRKLPTAL DGFSLEAMLT

IYQLHKICHS RAFQHWELIQ EDILDTGNDK NGKEEVIKRK

IPYILKRQLY ENKPRRPYIL KRDSYYY (Pro-Neurotensin 1-125 (large neuromedin N))
                                            SEQ ID NO. 15
SDSEEEMKAL EADFLTNMHT SKISKAHVPS WKMTLLNVCS

LVNNLNSPAE ETGEVHEEEL VARRKLPTAL DGFSLEAMLT

IYQLHKICHS RAFQHWELIQ EDILDTGNDK NGKEEVI KR

KIPYIL (neuromedin N)
                                            SEQ ID NO. 16
KIPYIL (neurotensin)
                                            SEQ ID NO. 17
pyroQLYENKPRRP YIL (Pro-Neurotensin 1-117)
                                            SEQ ID NO. 18
SDSEEEMKAL EADFLTNMHT SKISKAHVPS WKMTLLNVCS

LVNNLNSPAE ETGEVHEEEL VARRKLPTAL DGFSLEAMLT

IYQLHKICHS RAFQHWELIQ EDILDTGNDK NGKEEVI (Pro-Neurotensin 1-132)
                                            SEQ ID NO. 19
SDSEEEMKAL EADFLTNMHT SKISKAHVPS WKMTLLNVCS

LVNNLNSPAE ETGEVHEEEL VARRKLPTAL DGFSLEAMLT

IYQLHKICHS RAFQHWELIQ EDILDTGNDK NGKEEVIKRK

IPYILKRQLY EN (Pro-Neurotensin 120-140)
                                            SEQ ID NO. 20
KIPYILKRQL YENKPRRPYI L (Pro-Neurotensin 120-147)
                                            SEQ ID NO. 21
KIPYILKRQL YENKPRRPYIL KRDSYYY (Pro-Neurotensin 128-147)
                                            SEQ ID NO. 22
QLYENKPRRP YILKRDSYYY
```

In a specific embodiment the level of Pro-Neurotensin is measured with an immunoassay. More specifically an immunoassay is used as described in Ernst et al. (Peptides (2006), (27) 1787-1793). An immunoassay that may be useful for determining the level of Pro-Neurotensin or fragments thereof of at least 5 amino acids may comprise the steps as outlined in Example 3. All thresholds and values have to be seen in correlation to the test and the calibration used according to Example 3. A person skilled in the art may know that the absolute value of a threshold might be influenced by the calibration used. This means that all values and thresholds given herein are to be understood in context of the calibration used in herein (Example 3). A human Pro-Neurotensin-calibrator is available by ICI-Diagnostics, Berlin, Germany. Alternatively, the assay may also be calibrated by synthetic or recombinant P-NT 1-117 or fragments thereof (see also Ernst et al, 2006).

Binder that may be used for determining the level of Pro-Neurotensin or fragments thereof exhibit an affinity constant to Pro-Neurotensin or fragments thereof of at least $10^7$ $M^{-1}$, preferred $10^8$ $M^{-1}$, preferred affinity constant is greater than $10^9$ $M^{-1}$, most preferred greater than $10^{10}$ $M^{-1}$. A person skilled in the art knows that it may be considered to compensate lower affinity by applying a higher dose of compounds and this measure would not lead out-of-the-scope of the invention. Binding affinity may be determined using the Biacore method, offered as service analysis e.g. at Biaffin, Kassel, Germany, see also above.

The threshold for determining the risk of getting cancer in a subject or diagnosing cancer in a subject, in particular breast cancer in a female subject, according to the methods of the present invention is about or above 78 pmol/l PNT, preferred about or above 100 pmol/l, more preferred about or above 150 pmol/l. In a specific embodiment said threshold is about or above 100 pmol/l. These thresholds are related to the below mentioned calibration method. A PNT value above said threshold means that the subject has an enhanced risk of getting cancer or has already cancer In addition to the determination of the level of PTA, its splice variants or fragments thereof of at least 5 amino acids including Substance P and Neurokinin in a bodily fluid obtained from said subject; and/or the determination of the level of Pro-Neurotensin (PNT) or fragments thereof of at least 5 amino acids in a bodily fluid obtained from said subject; Pro-Enkephalin (PENK) or fragments of at least 5 amino acids thereof may be measured in a bodily fluid obtained from said subject. It has to be understood that in addition to the determination of the level of PTA, its splice variants or fragments thereof of at least 5 amino acids Pro-Enkephalin (PENK) or fragments of at least 5 amino acids thereof may be measured in a bodily fluid obtained from said subject. This means that the level of either PTA alone or in combination with either PENK or PNT is measured or a determination of PTA and PNT and PENK is combined and correlated with said risk.

In a more specific embodiment of the method according to the present invention the level Pro-Enkephalin (PENK) or fragments of at least 5 amino acids thereof is determined in addition to the determination of the level of Pro-Neurotensin 1-117 and in addition to the determination of PTA, its splice variants or fragments thereof.

Thus, subject matter of the present invention is also a method for predicting the risk of getting cancer in a subject that does not suffer from cancer or alternatively diagnosing cancer in a subject comprising:
  determining the level of PTA, its splice variants or fragments thereof of at least 5 amino acids, including Substance P and Neurokinin, in a bodily fluid obtained from said subject; and
  determining the level of Pro-Neurotensin or fragments thereof of at least 5 amino acids in a bodily fluid obtained from said subject; and/or
  determining the level of Pro-Enkephalin or fragments thereof of at least 5 amino acids in a bodily fluid obtained from said subject; and
  correlating said level of PTA, its splice variants or fragments thereof and Pro-Neurotensin or fragments thereof of at least 5 amino acids and/or the level of Pro-Enkephalin or fragments thereof of at least 5 amino acids with a risk for getting cancer,
  wherein an reduced level of PTA, its splice variants or fragments thereof is predictive for an enhanced risk of getting cancer or alternatively diagnosing cancer wherein an reduced level of PTA, its splice variants or fragments thereof is correlated with the diagnosis of cancer and wherein an increased level of Pro-Neurotensin and fragments thereof is predictive for an enhanced risk of getting cancer or alternatively diagnosing cancer wherein an increased level of Pro-Neurotensin and fragments thereof is correlated with the diagnosis of cancer and wherein a reduced level of Pro-Enkephalin or fragments thereof is predictive for an enhanced risk of getting cancer or alternatively diagnosing cancer wherein a reduced level of Pro-Enkephalin or fragments thereof is correlated with the diagnosis of cancer.

In particular said subject may be female and the cancer is breast cancer. The correlation between the above biomarker and biomarker combinations and breast cancer incidents in females is in particular remarkable and a specific embodiment for all methods according the present invention.

Pro-Enkephalin and fragments may have the following sequence:

(Pro-Enkephalin (1-243))
SEQ ID NO. 23
ECSQDCATCSYRLVRPADINFLACVMECEGKLPSLKIVVETCKELLQLSK

PELPQDGTSTLRENSKPEESHLLAKRYGGFMKRYGGFMKKMDELYPMEPE

EEANGSEILAKRYGGFMKKDAEEDDSLANSSDLLKELLETGDNRERSHHQ

DGSDNEEEVSKRYGGFMRGLKRSPQLEDEAKELQKRYGGFMRRVGRPEWW

MDYQKRYGGFLKRFAEALPSDEEGESYSKEVPEMEKRYGGF MRF

Fragments of Pro-Enkephalin that may be determined in a bodily fluid may be e.g. selected from the group of the following fragments:

(Syn-Enkephalin, Pro-Enkephalin 1-73)
SEQ ID NO. 24
ECSQDCATCSYRLVRPADINFLACVMECEGKLPSLKIWETCKELLQLSKP

ELPQDGTSTLRENSKPEESHLLA (Met-Enkephalin)
SEQ ID NO. 25
YGGFM (Leu-Enkephalin)
SEQ ID NO. 26
YGGFL (Pro-Enkephalin 90-109)
SEQ ID NO. 27
MDELYPMEPEEEANGSEILA (Pro-Enkephalin 119-159, Mid regional Pro-Enkephalin-fragment, MRPENK)
SEQ ID NO. 28
DAEEDDSLANSSDLLKELLETGDNRERSHHQDGSDNEEEVS (Met-Enkephalin-Arg-Gly-Leu)
SEQ ID NO. 29
YGGFMRGL (Pro-Enkephalin 172-183)
SEQ ID NO. 30
SPQLEDEAKELQ (Pro-Enkephalin 193-203)
SEQ ID NO. 9
VGRPEWWMDYQ (Pro-Enkephalin 213-234)
SEQ ID NO. 31
FAEALPSDEEGESYSKEVPEME (Pro-Enkephalin 213-241)
SEQ ID NO. 32
FAEALPSDEEGESYSKEVPEMEKRYGGF M (Met-Enkephalin-Arg-Phe)
SEQ ID NO. 33
YGGFMRF Determining the level of Pro-Enkephalin including Leu-Enkephalin and Met-Enkephalin or fragments thereof may mean that the immunoreactivity towards Pro-Enkephalin or fragments thereof including Leu-Enkephalin and Met-Enkephalin is determined. A binder used for determination of Pro-Enkephalin including Leu-Enkephalin and Met-Enkephalin or fragments thereof depending of the region of binding may bind to more than one of the above displayed molecules. This is clear to a person skilled in the art.

In a more specific embodiment of the method according to the present invention the level of MRPENK. (SEQ ID NO. 28: (Pro-Enkephalin 119-159, Mid regional Pro-Enkephalin-fragment, MRPENK) which is DAEEDDSLANSSDLLKELLETGDNRERSHHQDGSDNEEEVS is determined.

In a specific embodiment the level of Pro-Enkephalin or fragments thereof is measured with an immunoassay using antibodies or fragments of antibodies binding to Pro-Enkephalin or fragments thereof. An immunoassay that may be useful for determining the level of Pro-Enkephalin or fragments thereof of at least 5 amino acids may comprise the steps as outlined in Example 4. All thresholds and values have to be seen in correlation to the test and the calibration used according to Example 4. A person skilled in the art may know that the absolute value of a threshold might be influenced by the calibration used. This means that all values and thresholds given herein are to be understood in context of the calibration used in herein (Example 4).

According to the invention the diagnostic binder to pro-Enkephalin (and/or pro-Neurotensin and fragments thereof) is selected from the group consisting of antibodies e.g. IgG, a typical full-length immunoglobulin, or antibody fragments containing at least the F-variable domain of heavy and/or light chain as e.g. chemically coupled antibodies (fragment antigen binding) including but not limited to Fab-fragments including Fab minibodies, single chain Fab antibody, monovalent Fab antibody with epitope tags, e.g. Fab-V5Sx2; bivalent Fab (mini-antibody) dimerized with the CH3 domain; bivalent Fab or multivalent Fab, e.g. formed via multimerization with the aid of a heterologous domain, e.g. via dimerization of dHLX domains, e.g. Fab-dHLX-FSx2; F(ab')2-fragments, scFv-fragments, multimerized multivalent or/and multispecific scFv-fragments, bivalent and/or bispecific diabodies, BITE® (bispecific T-cell engager), trifunctional antibodies, polyvalent antibodies, e.g. from a different class than G; single-domain antibodies, e.g. nanobodies derived from camelid or fish immunoglobulines.

In a specific embodiment the level of Pro-Enkephalin or fragments thereof ((and/or Neurotensin and fragments thereof)) are measured with an assay using binders selected from the group comprising aptamers, non-Ig scaffolds as described in greater detail below binding to Pro-Enkephalin or fragments thereof.

Binder that may be used for determining the level of Pro-Enkephalin or fragments (and/or Pro-Neurotensin and fragments thereof) thereof exhibit an affinity constant to Pro-Enkephalin (and/or Pro-Neurotensin and fragments thereof) of at least $10^7$ $M^{-1}$, preferred $10^8$ $M^{-1}$, preferred affinity constant is higher than $10^9$ $M^{-1}$, most preferred more than $10^{10}$ $M^{-1}$. A person skilled in the art knows that it may be considered to compensate lower affinity by applying a higher dose of compounds and this measure would not lead out-of-the-scope of the invention. Binding affinity may be determined using the Biacore method, offered as service analysis e.g. at Biaffin, Kassel, Germany, see also above.

A human Pro-Enkephalin control human sample is available by ICI-Diagnostics, Berlin, Germany. The assay may also be calibrated by synthetic (for our experiments we used synthetic MRPENK, SEQ ID NO. 28) or recombinant Pro-Enkephalin or fragments thereof.

The Pro-Enkephalin (PENK) threshold for determining the risk of getting cancer, in particular breast cancer, in a subject or diagnosing cancer, in particular breast cancer, in a subject according to the methods of the present invention is about or below 100 pmol/l, preferably about or below 75 pmol/L, preferably about or below 50 pmol/L, preferably about 40.4 pmol/L. In a specific embodiment said threshold is about 40.4 pmol/l. These thresholds are related to the below mentioned calibration method. A PENK value below said threshold means that the subject has an enhanced risk of getting cancer or has already cancer.

In one embodiment of the invention said method is performed more than once in order to monitor the risk of getting cancer in a subject, in particular breast cancer in a female subject, or in order to monitor the course of treatment. In one specific embodiment said monitoring is performed in order to evaluate the response of said subject to preventive and/or therapeutic measures taken.

In one embodiment of the invention the method is used in order to stratify said subjects, in particular female subjects, into risk groups.

Subject of the present invention is also a method for predicting the risk of getting cancer in a subject, in particular breast cancer in a female subject, or identifying a subject, in particular a female subject, having an enhanced risk for getting cancer, in particular breast cancer, according to any of the preceding embodiments, wherein the level of Pro-Tachykinin, its splice variants or fragments thereof of at least 5 amino acids in a bodily fluid obtained from said subject either alone or in conjunction with other predictive laboratory or clinical parameters is used for the prediction of a subject's risk for getting cancer by a method which may be selected from the following alternatives:
- Comparison with the median of the level of Pro-Tachykinin, its splice variants or fragments thereof of at least 5 amino acids in a bodily fluid obtained from said subject in an ensemble of pre-determined samples in a population of "healthy" or "apparently healthy" subjects,
- Comparison with a quantile of the level of Pro-Tachykinin, its splice variants or fragments thereof of at least 5 amino acids in a bodily fluid obtained from said subject in an ensemble of pre-determined samples in a population of "healthy" or "apparently healthy" subjects,
- Calculation based on Cox Proportional Hazards analysis or by using Risk index calculations such as the NRI (Net Reclassification Index) or the IDI (Integrated Discrimination Index).

In one embodiment of the invention said method is performed more than once in order to monitor the risk of getting cancer in a subject, in particular breast cancer in a female subject, or in order to monitor the course of treatment. In one specific embodiment said monitoring is performed in order to evaluate the response of said subject to preventive and/or therapeutic measures taken.

In one embodiment of the invention the method is used in order to stratify said subjects into risk groups.

In one embodiment of the invention the cancer is selected from the group comprising breast cancer, and lung cancer.

SEQUENCE LISTING

The material in the ASCII text file created and filed by EFS-Web on Jun. 27, 2018, named "sequence listing" and having a size of 18 kB is incorporated herein by reference.

FIGURE DESCRIPTION

FIG. 1: shows a typical PTA dose/signal curve. Standard curve PTA.

Figure 2:
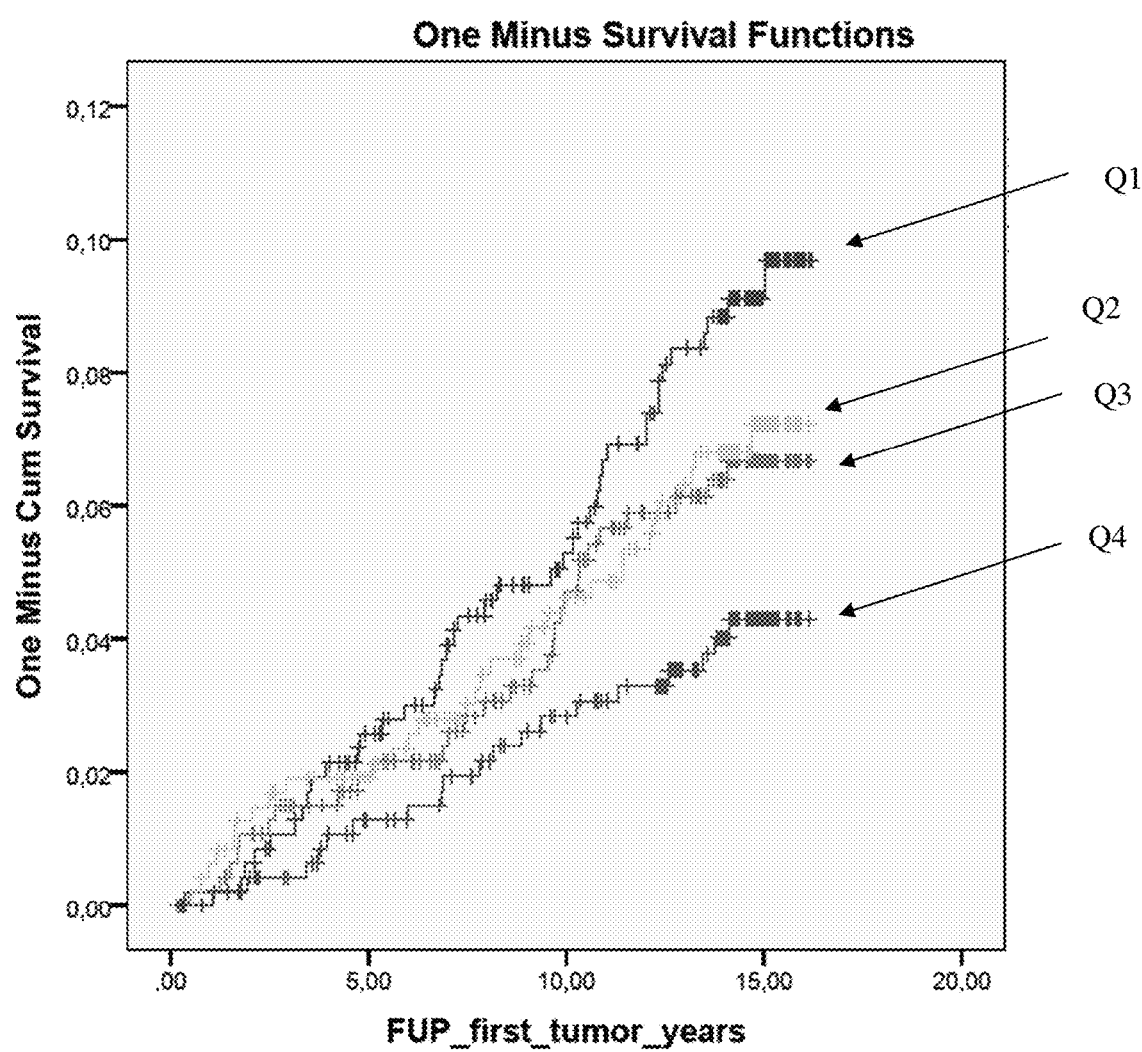

FIG. 2: Kaplan Meier graphs, illustrating the cumulative breast cancer diagnosis in women quartile (Q) 1 (below 45.6 pmol/l) quartile 2 (45.6-55.3 pmol/l), quartile 3 (55.4-65.9 pmol/l), quartile 4 (above 65.9 pmol/l). Decreased PTA indicates an increased long term risk of breast cancer development. Since any women with cancer history at day of baseline (blood sampling) were excluded, PTA is highly predictive for future breast cancer development. Over all, women from Q 1 have more than 2.1 times higher risk to develop breast cancer than women from Q 4.

Figure 3:
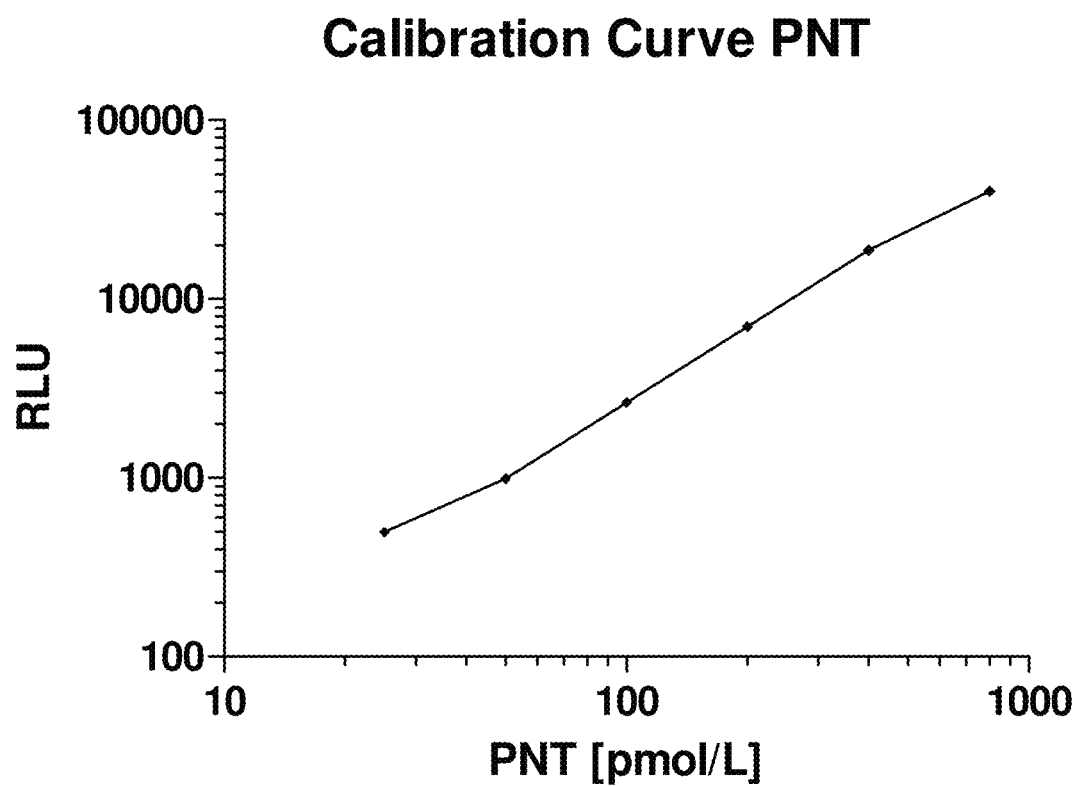

FIG. 3: shows a typical PNT dose/signal curve. Standard curve PNT

Figure 4:
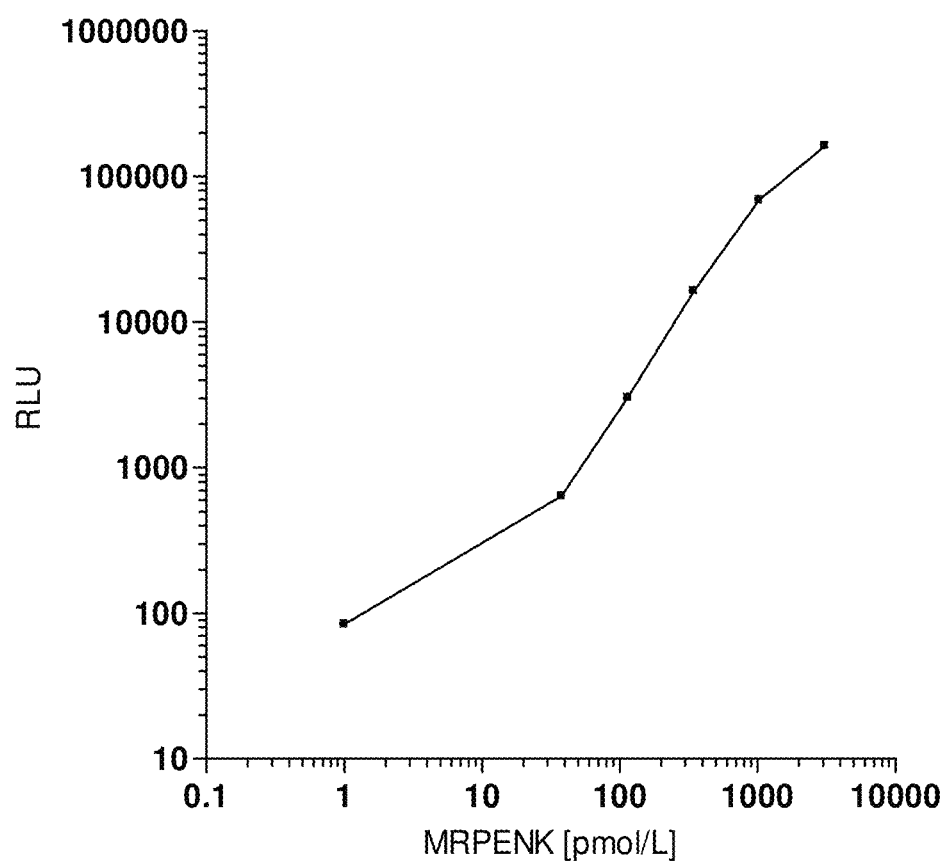

FIG. 4: shows a typical MR PENK dose/signal curve. Standard curve MR PENK

Figure 5:
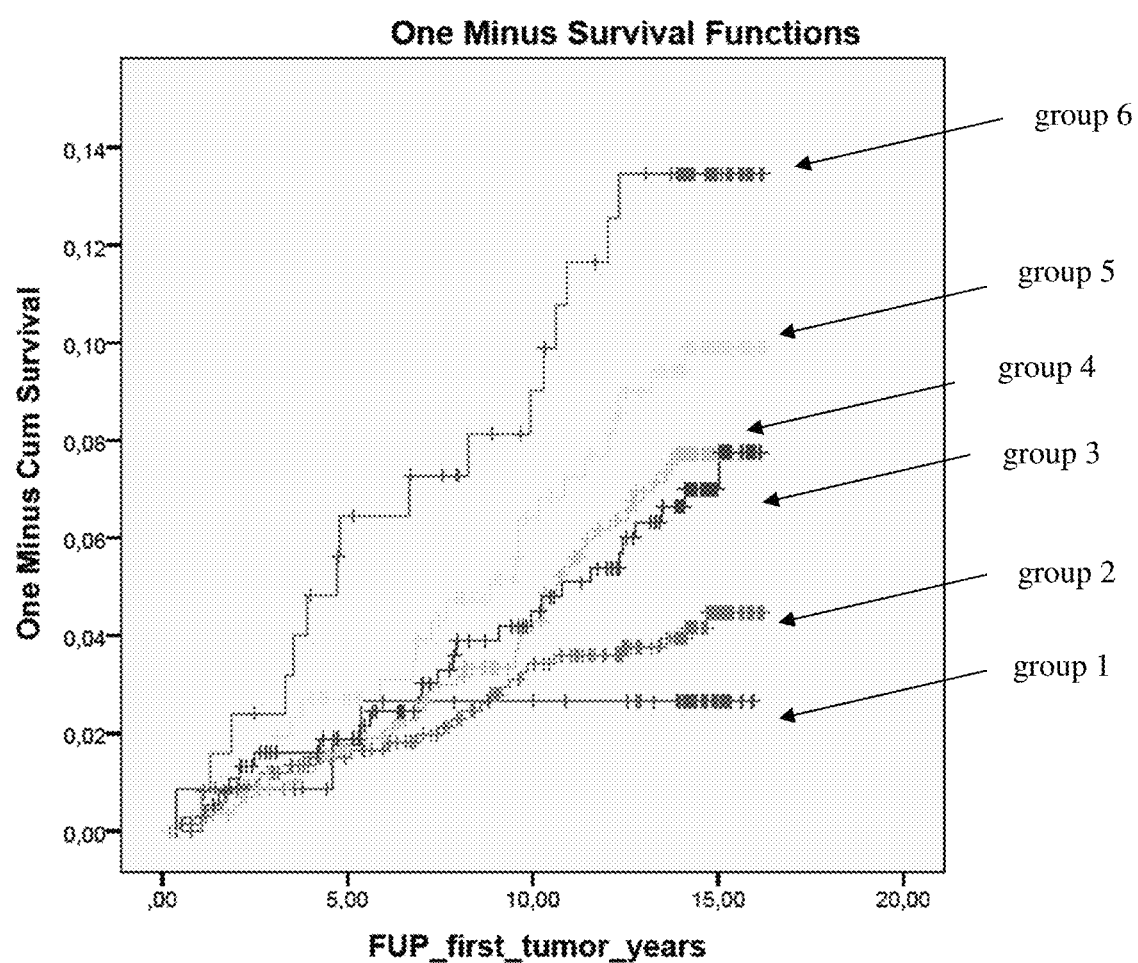

FIG. 5: Illustration example of combined analysis of PTA and PNT for breast cancer prediction the risk groups are displayed as defined in Table 9.

EXAMPLES

Example 1 PTA-immunoassay

Development of Anti PTA Antibodies
Peptides/Conjugates for Immunization:
Peptides for immunization were synthesized OPT Technologies, Berlin, Germany) with an additional N-terminal Cystein residue for conjugation of the peptides to bovine serum albumin (BSA). The peptides were covalently linked to BSA by using Sulfo-SMCC (Perbio-science, Bonn, Germany). The coupling procedure was performed according to the manual of Perbio.

TABLE 1

| Peptide for immunization | PTA Sequence |
|---|---|
| (C)GANDDLNYWSDWYDSDQIK | 3-22 (SEQ ID NO. 12) |
| (C)IKEELPEPFEHLLQRI | 21-36 (SEQ ID NO. 13) |

The antibodies were generated according to the following method:

A BALB/c mouse was immunized with 100 µg peptide-BSA-conjugate at day 0 and 14 (emulsified in 100 µl complete Freund's adjuvant) and 50 µg at day 21 and 28 (in 100 µl incomplete Freund's adjuvant). Three days before the fusion experiment was performed, the animal received 50 µg of the conjugate dissolved in 100 µl saline, given as one intraperitonal and one intravenous injection.

Splenocytes from the immunized mouse and cells of the myeloma cell line SP2/0 were fused with 1 ml 50% polyethylene glycol for 30 s at 37° C. After washing, the cells were seeded in 96-well cell culture plates. Hybrid clones were selected by growing in HAT medium [RPMI 1640 culture medium supplemented with 20% fetal calf serum and HAT-supplement]. After two weeks the HAT medium is replaced with HT Medium for three passages followed by returning to the normal cell culture medium.

The cell culture supernatants were primary screened for antigen specific IgG antibodies three weeks after fusion. The positive tested microcultures were transferred into 24-well plates for propagation. After retesting the selected cultures were cloned and recloned using the limiting-dilution technique and the isotypes were determined.

(Lane, R. D. "A short-duration polyethylene glycol fusiontechnique for increasing production of monoclonal antibody-secreting hybridomas", J. Immunol. Meth. 81: 223-228; (1985), Ziegler, B. et al. "Glutamate decarboxylase (GAD) is not detectable on the surface of rat islet cells examined by cytofluorometry and complement-dependent antibody-mediated cytotoxicity of monoclonal GAD antibodies", Horm. Metab. Res. 28: 11-15, (1996)).

Monoclonal Antibody Production

Antibodies were produced via standard antibody production methods (Marx et al., Monoclonal Antibody Production (1997), ATLA 25, 121) and purified via Protein A-chromatography. The antibody purities were >95% based on SDS gel electrophoresis analysis.

Labelling and Coating of Antibodies.

All antibodies were labelled with acridinium ester according the following procedure:

Labelled compound (tracer, anti PTA 3-22): 100 µg (100 µl) antibody (1 mg/ml in PBS, pH 7.4, was mixed with 10 µl Acridinium NHS-ester (1 mg/ml in acetonitrile, InVent GmbH, Germany) (EP 0353971) and incubated for 20 min at room temperature. Labelled antibody was purified by gel-filtration HPLC on Bio-Sil SEC 400-5 (Bio-Rad Laboratories, Inc., USA) The purified labelled antibody was diluted in (300 mmol/l potassiumphosphate, 100 mmol/l NaCl, 10 mmol/l Na-EDTA, 5 g/l bovine serum albumin, pH 7.0). The final concentration was approx. 800.000 relative light units (RLU) of labelled compound (approx. 20 ng labeled antibody) per 200 µl. Acridiniumester chemiluminescence was measured by using an AutoLumat LB 953 (Berthold Technologies GmbH & Co. KG).

Solid Phase Antibody (Coated Antibody):

Solid phase: Polystyrene tubes (Greiner Bio-One International AG, Austria) were coated (18 h at room temperature) with anti PTA 22-36 antibody (1.5 µg antibody/0.3 ml 100 mmol/l NaCl, 50 mmol/l Tris/HCl, pH 7.8). After blocking with 5% bovine serum albumine, the tubes were washed with PBS, pH 7.4 and vacuum dried.

PTA Immunoassay:

50 µl of sample (or calibrator) was pipetted into coated tubes, after adding labeled antibody (200ul), the tubes were incubated for 2 h at 18-25° C. Unbound tracer was removed by washing 5 times (each 1 ml) with washing solution (20 mmol/1 PBS, pH 7.4, 0.1% TRITON™ X-100 nonionic surfactant). Tube-bound labelled antibody was measured by using a Luminumeter LB 953, Berthold, Germany.

Calibration:

The assay was calibrated, using dilutions of synthetic P37, diluted in 20 mM K2PO4, 6 mM EDTA, 0.5% BSA, 50 µM Amastatin, 100 µM Leupeptin, pH 8.0. PTA control plasma is available at ICI-diagnostics, Berlin, Germany.

FIG. 1 shows a typical PTA dose/signal curve.

The analytical assay sensitivity was (the median signal generated by 20 determinations of 0-calibrator (no addition of PTA)+2SD2 standard deviations (SD), the corresponding PTA concentration is calculated from a standard curve) 4.4 pmol/L.

Example 2 Population Study/PTA

Methods

We measured PTA in fasting plasma from 2559 female participants of the population based Malmö Diet and Cancer Study baseline exam in 1991-1994 (age 58±6 years). We used multivariable adjusted (all traditional cardiovascular risk factors, diabetes risk factors and in analyses of cancer also heredity for cancer) Cox proportional hazards models to relate baseline PTA (hazard ratio per each standard deviation increase of log-transformed PTA) to the time to the first event of each of the studied endpoints during a median follow-up time of more than 12 years. Endpoints were retrieved through the Swedish National Hospital Discharge Registry, the Swedish Myocardial Infarction Registry, the Stroke in Malmö Registry and the Swedish Cancer Registry. Retrieval of endpoints through these registries has been validated and found to be accurate (see also Belting et al. Cancer Epidemiol Biomarkers Prev; 1-10. 2012 AACR). Insulin was measured by standard laboratory methods.

TABLE 2

Clinical characteristics of females in the study: Descriptive Statistics

| | N | Mean | Std. Deviation |
|---|---|---|---|
| Age at MDCS screening | 2559 | 57.554 | 5.9403 |
| Systolic blood pressure (mmHg) | 2559 | 140.50 | 19.311 |
| Diastolic blood pressure (mmHg) | 2559 | 85.65 | 9.117 |
| body-mass-index (weight/kg × kg) | 2559 | 25.5196 | 4.19083 |
| WAIST (cm) | 2559 | 76.99 | 10.245 |
| Glucose (mmol/l) | 2559 | 5.0418 | 1.21798 |
| Triglycerides (mmol/l) | 2559 | 1.2245 | .58404 |
| High density lipoprotein (mmol/l) | 2559 | 1.5123 | .36949 |
| Low density lipoprotein (mmol/l) | 2559 | 4.2016 | 1.04762 |
| P-Insulin | 2512 | 7.223 | 5.4223 |

Distribution of PTA in the Females Population (N=2559):

The mean value of PTA in the female population was 54.3 pmol/L, standard deviation+/−1.4 pmol/L. All results were within the measurement range of the assay, the lowest PTA concentration was 9.1 pmol/L. These results indicating the suitability of the used assay (assay sensitivity 4.4 pmol/L).

PTA and Prediction of Breast Cancer

We assessed the relationship between PTA and breast cancer (Table 3). All women with previous cancer (N=459) were excluded from the evaluation. There was a strong relationship between PTA and breast cancer in females. In a fully adjusted model each SD of decrease of PTA (we used reversed quartiles, revPTA, see table 3/4) was associated with a 28.2% increased risk of future breast cancer (table 3) and the top versus bottom quartile of PTA identified a more than 2.1-fold difference in risk of breast cancer (see table 5 and FIG. 2). Insulin without PTA in the equation was not significantly associated with future breast cancer development, but, surprisingly, if PTA is part of the equation Insulin became significant (p=0.035). Increased Insulin was associated with a 34.6% decrease risk per SD of future breast cancer. The predictive power of PTA was not influenced by Insulin.

TABLE 3

Variables in the Equation

|  | B | SE | Wald | df | Sig. | Exp (B) | 95.0% CI Lower |
|---|---|---|---|---|---|---|---|
| AGE | −.003 | .016 | .035 | 1 | .851 | .997 | .966 |
| BMI_B | .027 | .025 | 1.194 | 1 | .275 | 1.027 | .979 |
| LNINS | −.423 | .200 | 4.465 | 1 | .035 | .655 | .442 |
| HER_CANCER_0 | −.006 | .184 | .001 | 1 | .973 | .994 | .693 |
| Q_REV_PTA | .249 | .085 | 8.629 | 1 | .003 | 1.282 | 1.086 |

TABLE 4

PTA Quartile analysis:

| Quartile | Rev Quartile | N | Concentration range (pmol PTA/l) |
|---|---|---|---|
| 1 | 4 | 535 | <45.6 |
| 2 | 3 | 535 | 45.6-55.3 |
| 3 | 2 | 535 | 55.4-65.9 |
| 4 | 1 | 535 | >65.9 |

TABLE 5

Multivariate Cox proportional Hazards models for baseline PTA versus incidence of breast cancer.

|  | HR per 1 SD | P-value | Quartile 4 | Quartile 3 | Quartile 2 | Quartile 1 |
|---|---|---|---|---|---|---|
| Women (2140/137) | 1.22 (0.84-1.67) | 0.013 | 1.0 (ref) | 1.60 (1.21-2.22) | 1.6 (1.24-2.27) | 2.2 (1.82-3.6) |

Example 3

Pro-Neurotensin Assay

Antibodies were generated as described above. The antibody for labelling (LA) was generated against P-NT 1-19 (H-CSDSEEEMKALEADFLTNMH (SEQ ID NO. 33)) and the solid phase antibody (SPA) was generated against peptide P-NT 44-62 (CNLNSPAEETGEVHEEELVA (SEQ ID NO. 34). Antibody development and -production was performed as described above.

Immunoassay for the Quantification of Human Pro-Neurotensin

The technology used was a sandwich coated tube luminescence immunoassay, based on Acridinium ester labelling.

Labelled compound (tracer): 100 μg (100 μl) LA (1 mg/ml in PBS, pH 7.4, was mixed with 10 μl Acridinium NHS-ester (1 mg/ml in acetonitrile, InVent GmbH, Germany) (EP 0353971) and incubated for 20 min at room temperature. Labelled LA was purified by gel-filtration HPLC on Bio-Sil SEC 400-5 (Bio-Rad Laboratories, Inc., USA) The purified LA was diluted in (300 mmol/l potassiumphosphate, 100 mmol/l NaCl, 10 mmol/l Na-EDTA, 5 g/l bovine serum albumin, pH 7.0). The final concentration was approx. 800.000 relative light units (RLU) of labelled compound (approx. 20 ng labeled antibody) per 200 μl. Acridiniumester chemiluminescence was measured by using an AutoLumat LB 953 (Berthold Technologies GmbH & Co. KG).

Solid phase: Polystyrene tubes (Greiner Bio-One International AG, Austria) were coated (18 h at room temperature) with SPA (1.5 μg SPA/0.3 ml 100 mmol/l NaCl, 50 mmol/l Tris/HCl, pH 7.8). After blocking with 5% bovine serum albumine, the tubes were washed with PBS, pH 7.4 and vakuum dried.

Calibration:

The assay was calibrated, using dilutions of Pro-Neurotensin containing human serum. A pool of human sera with high Pro-Neurotensin immunoreactivity (InVent Diagostika, Hennigsdorf, Germany) was diluted with horse serum (Biochrom AG, Deutschland) (assay standards).

The standards were calibrated by use of the human Pro-Neurotensin-calibrator (ICI-Diagnostics, Berlin, Germany). Alternatively, the assay may be calibrated by synthetic or recombinant P-NT 1-117 or fragments thereof (see also Ernst et al., 2006).

ProNT Immunoassay:

50 μl of sample (or calibrator) was pipetted into SPA coated tubes, after adding labelled LA (200ul), the tubes were incubated for 16-22 h at 18-25° C. Unbound tracer was removed by washing 5 times (each 1 ml) with washing solution (20 mmol/l PBS, pH 7.4, 0.1% TRITON™ X-100 nonionic surfactant). Tube-bound LA was measured by using a Luminometer LB 953. Results were calculated from the calibration curve. A typical calibration curve is shown in FIG. 3.

Example 4

Pro-Enkephalin Immunoassay
Development of Antibodies
Peptides/Conjugates for Immunization:

Peptides for immunization were synthesized OPT Technologies, Berlin, Germany) with an additional N-terminal Cystein residue for conjugation of the peptides to bovine serum albumin (BSA). The peptides were covalently linked to BSA by using Sulfo-SMCC (Perbio-science, Bonn, Germany). The coupling procedure was performed according to the manual of Perbio.

TABLE 6

| Peptide for immunization | Pro-Enkephalin-sequence |
|---|---|
| (C)LKELLETG (SEQ ID NO. 35) | 133-140 |
| (C)SDNEEEVS (SEQ ID NO. 36) | 152-159 |

The antibodies were generated according to the following method:

A BALB/c mouse was immunized with 100 μg peptide-BSA-conjugate at day 0 and 14 (emulsified in 100 μl complete Freund's adjuvant) and 50 μg at day 21 and 28 (in 100 μl incomplete Freund's adjuvant). Three days before the fusion experiment was performed, the animal received 50 μg of the conjugate dissolved in 100 μl saline, given as one intraperitonal and one intravenous injection.

Splenocytes from the immunized mouse and cells of the myeloma cell line SP2/0 were fused with 1 ml 50% polyethylene glycol for 30 s at 37° C. After washing, the cells were seeded in 96-well cell culture plates. Hybrid clones were selected by growing in HAT medium [RPMI 1640 culture medium supplemented with 20% fetal calf serum and HAT-supplement]. After two weeks the HAT medium is replaced with HT Medium for three passages followed by returning to the normal cell culture medium.

The cell culture supernatants were primary screened for antigen specific IgG antibodies three weeks after fusion. The positive tested microcultures were transferred into 24-well plates for propagation. After retesting the selected cultures were cloned and recloned using the limiting-dilution technique and the isotypes were determined.

(Lane, R. D. "A short-duration polyethylene glycol fusiontechnique for increasing production of monoclonal antibody-secreting hybridomas", J. Immunol. Meth. 81: 223-228; (1985), Ziegler, B. et al. "Glutamate decarboxylase (GAD) is not detectable on the surface of rat islet cells examined by cytofluorometry and complement-dependent antibody-mediated cytotoxicity of monoclonal GAD antibodies", Horm. Metab. Res. 28: 11-15, (1996)).

TABLE 7

| Peptide for immunization | Pre-Pro-Enkephalin-sequence | Antibody name |
|---|---|---|
| (C)LKELLETG (SEQ ID NO. 35) | 133-140 | MR-MRPENK (used as coated tube antibody) |
| (C)SDNEEEVS (SEQ ID NO. 36) | 152-159 | CT-MRPENK (used as labelled antibody) |

Monoclonal Antibody Production

Antibodies were produced via standard antibody production methods (Marx et al., Monoclonal Antibody Production (1997), ATLA 25, 121) and purified via Protein A-chromatography. The antibody purities were >95% based on SDS gel electrophoresis analysis.

Labelling and Coating of Antibodies.

Labelled compound (tracer, CT-MRPENK antibody): 100 µg (100 µl) antibody (1 mg/ml in PBS, pH 7.4), was mixed with 10 µl Acridinium NHS-ester (1 mg/ml in acetonitrile, InVent GmbH, Germany) (EP 0353971) and incubated for 20 min at room temperature. Labelled antibody was purified by gel-filtration HPLC on Bio-Sil SEC 400-5 (Bio-Rad Laboratories, Inc., USA) The purified labelled antibody was diluted in (300 mmol/l potassiumphosphate, 100 mmol/l NaCl, 10 mmol/l Na-EDTA, 5 g/l bovine serum albumin, pH 7.0). The final concentration was approx. 800.000 relative light units (RLU) of labelled compound (approx. 20 ng labeled antibody) per 200 µl. Acridiniumester chemiluminescence was measured by using an AutoLumat LB 953 (Berthold Technologies GmbH & Co. KG).

Solid Phase Antibody (Coated Tube Antibody, MR-MRPENK Antibody):

Solid phase: Polystyrene tubes (Greiner Bio-One International AG, Austria) were coated (18 h at room temperature) with antibody (1.5 µg antibody/0.3 ml 100 mmol/l NaCl, 50 mmol/l Tris/HCl, pH 7.8). After blocking with 5% bovine serum albumine, the tubes were washed with PBS, pH 7.4 and vacuum dried.

Pro-Enkephalin Immunoassay:

50 µl of sample (or calibrator) was pipetted into coated tubes, after adding labelled antibody (200ul), the tubes were incubated for 2 h at 18-25° C. Unbound tracer was removed by washing 5 times (each 1 ml) with washing solution (20 mmol/l PBS, pH 7.4, 0.1% TRITON™ X-100 nonionic surfactant). Tube-bound labelled antibody was measured by using the Luminometer 953.

Calibration:

The assay was calibrated, using dilutions of synthetic MRPENK, diluted in 20 mM K2PO4, 6 mM EDTA, 0.5% BSA, 50 µM Amastatin, 100 µM Leupeptin, pH 8.0. Pro-Enkephalin control plasma is available at ICI-diagnostics, Berlin, Germany.

FIG. 4 shows a typical Pro-Enkephalin dose/signal curve.

The assay sensitivity (20 determinations of 0-calibrator (no addition of MRPENK)+2SD) was 5.5 pmol/L.

Example 5

Combination Analysis of PTA, Pro Neurotensin and HRT and, PTA, Pro-Neurotensin, Pro-Enkephalin and Insulin for Breast Cancer Prediction Since increasing Pro-Neurotensin and Pro-Enkephalin recently were shown to be highly predictive for breast cancer, we combined these biomarkers for breast cancer prediction. We added HRT (Hormone replacement therapy) as known risk factor for breast cancer to show the incremental value of PTA.

First, we combined PTA/ProNeurotensin/HRT/Insulin:

There was no significant correlation between PTA and Pro-Neurotensin (p=0.71). In a combined model including Insulin and hormone replacement therapy (HRT) using PTA and PNT (Table 8), we found them both independent in breast cancer prediction. Both markers were highly significant (p=0.005 for PTA and p<0.001 for PNT).

In a fully adjusted model each SD increase of PNT was associated with a 45.5% risk increase of future breast cancer. Each SD increase of PTA was associated with a 18.9% decreased risk (per SD) of future breast cancer.

HRT, as expected, was significant in the same model, but Insulin, surprisingly, was on top predicting breast cancer (p=0.027). Each SD increase of Insulin was associated with a 35.7% decrease of future breast cancer.

These data show that PTA, PNT, Insulin and HRT, each add significant information for breast cancer prediction.

TABLE 8 combined analysis of PNT and PTA for breast cancer prediction.
Variables in the Equation

| | B | SE | Wald | df | Sig. | Exp (B) | 95.0% CI Lower |
|---|---|---|---|---|---|---|---|
| AGE | −.004 | .016 | .048 | 1 | .826 | .996 | .966 |
| BMI_B | .029 | .025 | 1.342 | 1 | .247 | 1.029 | .980 |
| LNINS | −.441 | .199 | 4.889 | 1 | .027 | .643 | .435 |
| hrt_curr | .612 | .197 | 9.656 | 1 | .002 | 1.844 | 1.254 |
| HER_CANCER_0 | .014 | .184 | .006 | 1 | .938 | 1.014 | .707 |
| ZLN_PTA | −.210 | .075 | 7.925 | 1 | .005 | .811 | .700 |
| ZLN_PNT | .375 | .089 | 17.938 | 1 | .000 | 1.455 | 1.223 |

In a Kaplan Meier analysis we illustrate the combinatory information of PTA and PNT, Table 9 and FIG. 5:

We combined quartiles of PTA and PNT:

Since low PTA values indicating an increased risk of breast cancer development, we reversed the PTA quartiles (revPTA): $1^{st}$ quartile PTA=$4^{th}$ quartile revPTA; $2^{nd}$ quartile PTA=$3^{rd}$ quartile revPTA; $3^{rd}$ quartile PTA=$2^{nd}$ quartile revPTA; $4^{th}$ quartile PTA=$1^{st}$ quartile revPTA. (Table 9)

TABLE 9

| revPTA/PNT | N of subjects | 15 year breast cancer development | risk (%) | Relative risk (lowest risk group = 1) |
|---|---|---|---|---|
| Q1/Q1 (group 1) | 117 | 3 | 2.6 | 1 |
| Q1/Q2 and Q2/Q1 Q1/Q3 Q2/Q2 Q3/Q1 (group 2) | 673 | 27 | 4.0 | 1.54 |
| Q1/Q4 Q2/Q3 Q3/Q2 Q4/Q1 (group 3) | 583 | 42 | 7.2 | 2.8 |
| Q2/Q4 Q3/Q3 Q4/Q2 (group 4) | 377 | 25 | 6.6 | 2.5 |
| Q3/Q4 Q4/Q3 (group 5) | 263 | 24 | 9.1 | 3.5 |
| Q4/Q4 (group 6) | 127 | 16 | 12.6 | 4.9 |

Combining highest quartile of PNT and lowest PTA quartile (group 6) vs. lowest PNT- and highest PTA quartile (group 1) showed a combined risk of 4.9 for future breast cancer (see FIG. 5).

Combined Analysis of PTA, Pro Enkephalin, HRT, Insulin and PNT in the Female Population:

There was a significant correlation between PTA and Pro-Enkephalin (p=<0.001, r=0.35). In a combined model including Insulin, PTA, PNT and Pro-Enkephalin, we found all markers independently adding information for breast cancer prediction (Table 10). All markers were highly significant (p=0.028 for PTA, p<0.001 for PNT, p=0.009 for Insulin and p<0.001 for Pro Enkephalin). PTA remains independent although it is highly correlated to Pro Enkephalin. In a fully adjusted model each SD increase of PNT was associated with a 47.8% risk increase of future breast cancer. Increase of PTA was associated with a 15.8% decreased risk (per SD) of future breast cancer. Increase of Pro-Enkephalin was associated with a decreased risk of 26.4% (per SD)- and increase of Insulin was associated with a decreased risk of 40.4% (per SD) of future breast cancer.

These data show a strong independent and additive information on future breast cancer development by PTA, PNT, Pro-Enkephalin and Insulin.

TABLE 10 combined analysis of PTA, Pro-Enkephalin, Insulin and PNT.
Variables in the Equation

| | B | SE | Wald | df | Sig. | Exp (B) | 95.0% CI Lower |
|---|---|---|---|---|---|---|---|
| AGE | −.001 | .016 | .002 | 1 | .966 | .999 | .969 |
| BMI_B | .019 | .025 | .568 | 1 | .451 | 1.019 | .970 |
| LNINS | −.518 | .200 | 6.739 | 1 | .009 | .596 | .403 |
| HER_CANCER_0 | −.021 | .185 | .012 | 1 | .911 | .980 | .682 |
| ZLN_PTA | −.171 | .078 | 4.827 | 1 | .028 | .842 | .723 |
| ZLN_PNT | .390 | .089 | 19.328 | 1 | .000 | 1.478 | 1.242 |
| ZLN_PENK | −.309 | .087 | 12.655 | 1 | .000 | .734 | .619 |

The invention claimed is:

1. A method for predicting the risk of getting cancer in a subject that does not suffer from cancer comprising:
   determining the level of Pro-Tachykinin in a bodily fluid sample obtained from said subject by determining the level of binding to the region of Pro-Tachykinin that consists of Pro-Tachykinin 1-37 (SEQ ID NO. 2) by measuring the level with an immunoassay having an antibody specific to binding to SEQ ID NO. 2; and
   correlating said level of Pro-Tachykinin with risk for getting cancer, wherein a reduced level is predictive for an enhanced risk of getting cancer and said reduced level is a level below a threshold wherein said threshold is set at 100 pmol/l or below.

2. The method according to claim 1 further comprising the following steps:
   determining the level of Pro-Neurotensin in a bodily fluid obtained from said subject; and
   correlating additionally Pro-Neurotensin with a risk for getting cancer, wherein an increased level of 78 pmol/l or above of Pro-Neurotensin is predictive for an enhanced risk of getting cancer.

3. The method according to claim 1 further comprising the following steps:
   determining the level of Pro-Enkephalin in a bodily fluid obtained from said subject; and
   correlating additionally Pro-Enkephalin with a risk for getting cancer, and wherein a reduced level of 100 pmol/l or below of Pro-Enkephalin is predictive for an enhanced risk of getting cancer.

4. The method according to claim 1 further comprising the following steps:
   determining the level of Insulin in a bodily fluid obtained from said subject; and
   correlating additionally said level of Insulin with a risk for getting cancer, wherein a reduced level of 70 pmol/l or below of Insulin is predictive for an enhanced risk of getting cancer.

5. The method according to claim 2 wherein additionally correlating means a combined analysis of the determined biomarker levels by taking into account the relative risk factors for cancer development obtained by the individual biomarkers.

6. The method according to claim 1 wherein a reduced level of Pro-Tachykinin is a level below a threshold wherein said threshold is set at 80 pmol/L or below.

7. The method according to claim 2 wherein an increased level of Pro-Neurotensin is a level above a threshold wherein said threshold is 100 pmol/l.

8. The method according to claim 3 wherein a reduced level of Pro-Enkephalin is a level below a threshold wherein said threshold is 75 pmol/L.

9. The method according to claim 1 wherein said subject is female.

10. The method according to claim 9, wherein said cancer is breast cancer.

11. The method according to claim 1 wherein said cancer is lung cancer.

12. A The method according to claim 1, wherein said subject has never had a history of diagnosis of cancer at the time the sample of bodily fluid is taken from said subject.

13. The method according to claim 1, wherein said subject has had a history of diagnosis of cancer and has been cured at the time the sample of bodily fluid is taken from said subject and the risk of reoccurrence of getting cancer is determined or alternatively the reoccurrence of breast cancer is determined.

14. The method according to claim 1, wherein at the time the sample of bodily fluid is taken from said subject, said subject has been diagnosed as having a cardiovascular disease or diabetes.

15. The method according to claim 1, wherein additionally at least one clinical parameter is determined selected from: age, presence of diabetes mellitus, and current smoking.

16. The method according to claim 2, wherein the level of Pro-Neurotensin is measured with an immunoassay.

17. The method according to claim 1 wherein said method is performed more than once on the same subject later in time in order to monitor the risk of getting cancer in the subject or in order to monitor the course of treatment.

18. The method according to claim 17 wherein said monitoring is performed in order to evaluate the response of said subject to preventive and/or therapeutic measures taken.

19. The method according to claim 1, wherein multiple reduced level thresholds of Pro-Tachykinin are determined in order to stratify said subjects into multiple differing risk groups.

20. The method according to claim 1 wherein the bodily fluid is blood or plasma or serum.

21. The method according to claim 1 wherein a reduced level of Pro-Tachykinin is a level below a threshold wherein said threshold is set at 60 pmol/L or below.

22. The method according to claim 1 wherein a reduced level of Pro-Tachykinin is a level below a threshold wherein said threshold is set at 50 pmol/L or below.

23. The method according to claim 2 wherein an increased level of Pro-Neurotensin is a level above a threshold wherein said threshold is 150 pmol/l.

24. The method according to claim 3 wherein a reduced level of Pro-Enkephalin is a level below a threshold wherein said threshold is 50 pmol/L.

25. The method according to claim 3, wherein the level of Pro-Enkephalin is measured with an immunoassay.

26. The A method according to claim 4, wherein the level of Insulin is measured with an immunoassay.

27. The method according to claim 1, wherein the subject has a reduced level of Pro-Tachykinin below 100 pmol/l and the subject is given preventative or therapeutic treatment for cancer.

* * * * *

SEQUENCE LISTING

<160> NUMBER OF SEQ ID NOS: 37

<210> SEQ ID NO 1
<211> LENGTH: 110
<212> TYPE: PRT
<213> ORGANISM: Homo sapiens

<400> SEQUENCE: 1

Glu Glu Ile Gly Ala Asn Asp Asp Leu Asn Tyr Trp Ser Asp Trp Tyr
1               5                   10                  15

Asp Ser Asp Gln Ile Lys Glu Glu Leu Pro Glu Pro Phe Glu His Leu
            20                  25                  30

Leu Gln Arg Ile Ala Arg Arg Pro Lys Pro Gln Gln Phe Phe Gly Leu
        35                  40                  45

Met Gly Lys Arg Asp Ala Asp Ser Ser Ile Glu Lys Gln Val Ala Leu
    50                  55                  60

Leu Lys Ala Leu Tyr Gly His Gly Gln Ile Ser His Lys Arg His Lys
65                  70                  75                  80

Thr Asp Ser Phe Val Gly Leu Met Gly Lys Arg Ala Leu Asn Ser Val
                85                  90                  95

Ala Tyr Glu Arg Ser Ala Met Gln Asn Tyr Glu Arg Arg Arg
            100                 105                 110

<210> SEQ ID NO 2
<211> LENGTH: 37
<212> TYPE: PRT
<213> ORGANISM: Homo sapiens

<400> SEQUENCE: 2

-continued

Glu Ile Gly Ala Asn Asp Leu Asn Tyr Trp Ser Asp Trp Tyr
1               5                   10                  15

Asp Ser Asp Gln Ile Lys Glu Glu Leu Pro Glu Pro Phe Glu His Leu
            20                  25                  30

Leu Gln Arg Ile Ala
        35

<210> SEQ ID NO 3
<211> LENGTH: 11
<212> TYPE: PRT
<213> ORGANISM: Homo sapiens

<400> SEQUENCE: 3

Arg Pro Lys Pro Gln Gln Phe Phe Gly Leu Met
1               5                   10

<210> SEQ ID NO 4
<211> LENGTH: 36
<212> TYPE: PRT
<213> ORGANISM: Homo sapiens

<400> SEQUENCE: 4

Asp Ala Asp Ser Ser Ile Glu Lys Gln Val Ala Leu Leu Lys Ala Leu
1               5                   10                  15

Tyr Gly His Gly Gln Ile Ser His Lys Arg His Lys Thr Asp Ser Phe
            20                  25                  30

Val Gly Leu Met
        35

<210> SEQ ID NO 5
<211> LENGTH: 19
<212> TYPE: PRT
<213> ORGANISM: Homo sapiens

<400> SEQUENCE: 5

Gly His Gly Gln Ile Ser His Lys Arg His Lys Thr Asp Ser Phe Val
1               5                   10                  15

Gly Leu Met

<210> SEQ ID NO 6
<211> LENGTH: 10
<212> TYPE: PRT
<213> ORGANISM: Homo sapiens

<400> SEQUENCE: 6

His Lys Thr Asp Ser Phe Val Gly Leu Met
1               5                   10

<210> SEQ ID NO 7
<211> LENGTH: 16
<212> TYPE: PRT
<213> ORGANISM: Homo sapiens

<400> SEQUENCE: 7

Ala Leu Asn Ser Val Ala Tyr Glu Arg Ser Ala Met Gln Asn Tyr Glu
1               5                   10                  15

<210> SEQ ID NO 8
<211> LENGTH: 92
<212> TYPE: PRT
<213> ORGANISM: Homo sapiens

```
<400> SEQUENCE: 8

Glu Glu Ile Gly Ala Asn Asp Asp Leu Asn Tyr Trp Ser Asp Trp Tyr
1               5                   10                  15

Asp Ser Asp Gln Ile Lys Glu Glu Leu Pro Glu Pro Phe Glu His Leu
            20                  25                  30

Leu Gln Arg Ile Ala Arg Arg Pro Lys Pro Gln Gln Phe Phe Gly Leu
        35                  40                  45

Met Gly Lys Arg Asp Ala Asp Ser Ser Ile Glu Lys Gln Val Ala Leu
    50                  55                  60

Leu Lys Ala Leu Tyr Gly His Gly Gln Ile Ser His Lys Met Ala Tyr
65                  70                  75                  80

Glu Arg Ser Ala Met Gln Asn Tyr Glu Arg Arg
                85                  90

<210> SEQ ID NO 9
<211> LENGTH: 110
<212> TYPE: PRT
<213> ORGANISM: Homo sapiens

<400> SEQUENCE: 9

Glu Glu Ile Gly Ala Asn Asp Asp Leu Asn Tyr Trp Ser Asp Trp Tyr
1               5                   10                  15

Asp Ser Asp Gln Ile Lys Glu Glu Leu Pro Glu Pro Phe Glu His Leu
            20                  25                  30

Leu Gln Arg Ile Ala Arg Arg Pro Lys Pro Gln Gln Phe Phe Gly Leu
        35                  40                  45

Met Gly Lys Arg Asp Ala Asp Ser Ser Ile Glu Lys Gln Val Ala Leu
    50                  55                  60

Leu Lys Ala Leu Tyr Gly His Gly Gln Ile Ser His Lys Arg His Lys
65                  70                  75                  80

Thr Asp Ser Phe Val Gly Leu Met Gly Lys Arg Ala Leu Asn Ser Val
                85                  90                  95

Ala Tyr Glu Arg Ser Ala Met Gln Asn Tyr Glu Arg Arg
            100                 105                 110

<210> SEQ ID NO 10
<211> LENGTH: 77
<212> TYPE: PRT
<213> ORGANISM: Homo sapiens

<400> SEQUENCE: 10

Glu Glu Ile Gly Ala Asn Asp Asp Leu Asn Tyr Trp Ser Asp Trp Tyr
1               5                   10                  15

Asp Ser Asp Gln Ile Lys Glu Glu Leu Pro Glu Pro Phe Glu His Leu
            20                  25                  30

Leu Gln Arg Ile Ala Arg Arg Pro Lys Pro Gln Gln Phe Phe Gly Leu
        35                  40                  45

Met Gly Lys Arg Asp Ala Gly His Gly Gln Ile Ser His Lys Met Ala
    50                  55                  60

Tyr Glu Arg Ser Ala Met Gln Asn Tyr Glu Arg Arg
65                  70                  75

<210> SEQ ID NO 11
<211> LENGTH: 98
<212> TYPE: PRT
<213> ORGANISM: Homo sapiens

<400> SEQUENCE: 11
```

Glu Ile Gly Ala Asn Asp Asp Leu Asn Tyr Trp Ser Asp Trp Tyr
1               5                   10                  15

Asp Ser Asp Gln Ile Lys Glu Glu Leu Pro Glu Pro Phe Glu His Leu
            20                  25                  30

Leu Gln Arg Ile Ala Arg Arg Pro Lys Pro Gln Gln Phe Phe Gly Leu
        35                  40                  45

Met Gly Lys Arg Asp Ala Gly His Gly Gln Ile Ser His Lys Arg His
    50                  55                  60

Lys Thr Asp Ser Phe Val Gly Leu Met Gly Lys Arg Ala Leu Asn Ser
65                  70                  75                  80

Val Ala Tyr Glu Arg Ser Ala Met Gln Asn Tyr Glu Arg Arg Arg Ser
                85                  90                  95

Glu Gln

<210> SEQ ID NO 12
<211> LENGTH: 19
<212> TYPE: PRT
<213> ORGANISM: Homo sapiens

<400> SEQUENCE: 12

Gly Ala Asn Asp Asp Leu Asn Tyr Trp Ser Asp Trp Tyr Asp Ser Asp
1               5                   10                  15

Gln Ile Lys

<210> SEQ ID NO 13
<211> LENGTH: 16
<212> TYPE: PRT
<213> ORGANISM: Homo sapiens

<400> SEQUENCE: 13

Ile Lys Glu Glu Leu Pro Glu Pro Phe Glu His Leu Leu Gln Arg Ile
1               5                   10                  15

<210> SEQ ID NO 14
<211> LENGTH: 147
<212> TYPE: PRT
<213> ORGANISM: Homo sapiens

<400> SEQUENCE: 14

Ser Asp Ser Glu Glu Met Lys Ala Leu Ala Asp Phe Leu Thr
1               5                   10                  15

Asn Met His Thr Ser Lys Ile Ser Lys Ala His Val Pro Ser Trp Lys
                20                  25                  30

Met Thr Leu Leu Asn Val Cys Ser Leu Val Asn Asn Leu Asn Ser Pro
            35                  40                  45

Ala Glu Glu Thr Gly Glu Val His Glu Glu Glu Val Ala Arg Arg
    50                  55                  60

Lys Leu Pro Thr Ala Leu Asp Gly Phe Ser Leu Glu Ala Met Leu Thr
65                  70                  75                  80

Ile Tyr Gln Leu His Lys Ile Cys His Ser Arg Ala Phe Gln His Trp
                85                  90                  95

Glu Leu Ile Gln Glu Asp Ile Leu Asp Thr Gly Asn Asp Lys Asn Gly
            100                 105                 110

Lys Glu Glu Val Ile Lys Arg Lys Ile Pro Tyr Ile Leu Lys Arg Gln
        115                 120                 125

Leu Tyr Glu Asn Lys Pro Arg Arg Pro Tyr Ile Leu Lys Arg Asp Ser
    130                 135                 140

Tyr Tyr Tyr
145

<210> SEQ ID NO 15
<211> LENGTH: 125
<212> TYPE: PRT
<213> ORGANISM: Homo sapiens

<400> SEQUENCE: 15

Ser Asp Ser Glu Glu Met Lys Ala Leu Glu Ala Asp Phe Leu Thr
1               5                   10                  15

Asn Met His Thr Ser Lys Ile Ser Lys Ala His Val Pro Ser Trp Lys
                20                  25                  30

Met Thr Leu Leu Asn Val Cys Ser Leu Val Asn Asn Leu Asn Ser Pro
            35                  40                  45

Ala Glu Glu Thr Gly Glu Val His Glu Glu Leu Val Ala Arg Arg
        50                  55                  60

Lys Leu Pro Thr Ala Leu Asp Gly Phe Ser Leu Glu Ala Met Leu Thr
65                  70                  75                  80

Ile Tyr Gln Leu His Lys Ile Cys His Ser Arg Ala Phe Gln His Trp
                85                  90                  95

Glu Leu Ile Gln Glu Asp Ile Leu Asp Thr Gly Asn Asp Lys Asn Gly
            100                 105                 110

Lys Glu Val Ile Lys Arg Lys Ile Pro Tyr Ile Leu
        115                 120                 125

<210> SEQ ID NO 16
<211> LENGTH: 6
<212> TYPE: PRT
<213> ORGANISM: Homo sapiens

<400> SEQUENCE: 16

Lys Ile Pro Tyr Ile Leu
1               5

<210> SEQ ID NO 17
<211> LENGTH: 13
<212> TYPE: PRT
<213> ORGANISM: Homo sapiens

<400> SEQUENCE: 17

Gln Leu Tyr Glu Asn Lys Pro Arg Arg Pro Tyr Ile Leu
1               5                   10

<210> SEQ ID NO 18
<211> LENGTH: 117
<212> TYPE: PRT
<213> ORGANISM: Homo sapiens

<400> SEQUENCE: 18

Ser Asp Ser Glu Glu Met Lys Ala Leu Glu Ala Asp Phe Leu Thr
1               5                   10                  15

Asn Met His Thr Ser Lys Ile Ser Lys Ala His Val Pro Ser Trp Lys
                20                  25                  30

Met Thr Leu Leu Asn Val Cys Ser Leu Val Asn Asn Leu Asn Ser Pro
            35                  40                  45

Ala Glu Glu Thr Gly Glu Val His Glu Glu Leu Val Ala Arg Arg
        50                  55                  60

Lys Leu Pro Thr Ala Leu Asp Gly Phe Ser Leu Glu Ala Met Leu Thr

```
                65                  70                  75                  80
Ile Tyr Gln Leu His Lys Ile Cys His Ser Arg Ala Phe Gln His Trp
                    85                  90                  95
Glu Leu Ile Gln Glu Asp Ile Leu Asp Thr Gly Asn Asp Lys Asn Gly
            100                 105                 110
Lys Glu Glu Val Ile
            115
```

<210> SEQ ID NO 19
<211> LENGTH: 132
<212> TYPE: PRT
<213> ORGANISM: Homo sapiens

<400> SEQUENCE: 19

```
Ser Asp Ser Glu Glu Met Lys Ala Leu Glu Ala Asp Phe Leu Thr
1               5                   10                  15
Asn Met His Thr Ser Lys Ile Ser Lys Ala His Val Pro Ser Trp Lys
                20                  25                  30
Met Thr Leu Leu Asn Val Cys Ser Leu Val Asn Asn Leu Asn Ser Pro
            35                  40                  45
Ala Glu Glu Thr Gly Val His Glu Glu Leu Val Ala Arg Arg
        50                  55                  60
Lys Leu Pro Thr Ala Leu Asp Gly Phe Ser Leu Glu Ala Met Leu Thr
65                  70                  75                  80
Ile Tyr Gln Leu His Lys Ile Cys His Ser Arg Ala Phe Gln His Trp
                    85                  90                  95
Glu Leu Ile Gln Glu Asp Ile Leu Asp Thr Gly Asn Asp Lys Asn Gly
            100                 105                 110
Lys Glu Glu Val Ile Lys Arg Lys Ile Pro Tyr Ile Leu Lys Arg Gln
            115                 120                 125
Leu Tyr Glu Asn
        130
```

<210> SEQ ID NO 20
<211> LENGTH: 21
<212> TYPE: PRT
<213> ORGANISM: Homo sapiens

<400> SEQUENCE: 20

```
Lys Ile Pro Tyr Ile Leu Lys Arg Gln Leu Tyr Glu Asn Lys Pro Arg
1               5                   10                  15
Arg Pro Tyr Ile Leu
            20
```

<210> SEQ ID NO 21
<211> LENGTH: 28
<212> TYPE: PRT
<213> ORGANISM: Homo sapiens

<400> SEQUENCE: 21

```
Lys Ile Pro Tyr Ile Leu Lys Arg Gln Leu Tyr Glu Asn Lys Pro Arg
1               5                   10                  15
Arg Pro Tyr Ile Leu Lys Arg Asp Ser Tyr Tyr Tyr
            20                  25
```

<210> SEQ ID NO 22
<211> LENGTH: 20
<212> TYPE: PRT
<213> ORGANISM: Homo sapiens

<400> SEQUENCE: 22

Gln Leu Tyr Glu Asn Lys Pro Arg Arg Pro Tyr Ile Leu Lys Arg Asp
1               5                   10                  15

Ser Tyr Tyr Tyr
            20

<210> SEQ ID NO 23
<211> LENGTH: 243
<212> TYPE: PRT
<213> ORGANISM: Homo sapiens

<400> SEQUENCE: 23

Glu Cys Ser Gln Asp Cys Ala Thr Cys Ser Tyr Arg Leu Val Arg Pro
1               5                   10                  15

Ala Asp Ile Asn Phe Leu Ala Cys Val Met Glu Cys Glu Gly Lys Leu
            20                  25                  30

Pro Ser Leu Lys Ile Trp Glu Thr Cys Lys Glu Leu Leu Gln Leu Ser
        35                  40                  45

Lys Pro Glu Leu Pro Gln Asp Gly Thr Ser Thr Leu Arg Glu Asn Ser
    50                  55                  60

Lys Pro Glu Glu Ser His Leu Leu Ala Lys Arg Tyr Gly Gly Phe Met
65                  70                  75                  80

Lys Arg Tyr Gly Gly Phe Met Lys Lys Met Asp Glu Leu Tyr Pro Met
                85                  90                  95

Glu Pro Glu Glu Glu Ala Asn Gly Ser Glu Ile Leu Ala Lys Arg Tyr
            100                 105                 110

Gly Gly Phe Met Lys Lys Asp Ala Glu Glu Asp Asp Ser Leu Ala Asn
        115                 120                 125

Ser Ser Asp Leu Leu Lys Glu Leu Leu Glu Thr Gly Asp Asn Arg Glu
    130                 135                 140

Arg Ser His His Gln Asp Gly Ser Asp Asn Glu Glu Glu Val Ser Lys
145                 150                 155                 160

Arg Tyr Gly Gly Phe Met Arg Gly Leu Lys Arg Ser Pro Gln Leu Glu
                165                 170                 175

Asp Glu Ala Lys Glu Leu Gln Lys Arg Tyr Gly Gly Phe Met Arg Arg
            180                 185                 190

Val Gly Arg Pro Glu Trp Trp Met Asp Tyr Gln Lys Arg Tyr Gly Gly
        195                 200                 205

Phe Leu Lys Arg Phe Ala Glu Ala Leu Pro Ser Asp Glu Glu Gly Glu
    210                 215                 220

Ser Tyr Ser Lys Glu Val Pro Glu Met Glu Lys Arg Tyr Gly Gly Phe
225                 230                 235                 240

Met Arg Phe

<210> SEQ ID NO 24
<211> LENGTH: 73
<212> TYPE: PRT
<213> ORGANISM: Homo sapiens

<400> SEQUENCE: 24

Glu Cys Ser Gln Asp Cys Ala Thr Cys Ser Tyr Arg Leu Val Arg Pro
1               5                   10                  15

Ala Asp Ile Asn Phe Leu Ala Cys Val Met Glu Cys Glu Gly Lys Leu
            20                  25                  30

Pro Ser Leu Lys Ile Trp Glu Thr Cys Lys Glu Leu Leu Gln Leu Ser

```
            35                 40                 45
Lys Pro Glu Leu Pro Gln Asp Gly Thr Ser Thr Leu Arg Glu Asn Ser
    50                 55                 60

Lys Pro Glu Glu Ser His Leu Leu Ala
65                 70
```

<210> SEQ ID NO 25
<211> LENGTH: 5
<212> TYPE: PRT
<213> ORGANISM: Homo sapiens

<400> SEQUENCE: 25

```
Tyr Gly Gly Phe Met
1               5
```

<210> SEQ ID NO 26
<211> LENGTH: 5
<212> TYPE: PRT
<213> ORGANISM: Homo sapiens

<400> SEQUENCE: 26

```
Tyr Gly Gly Phe Leu
1               5
```

<210> SEQ ID NO 27
<211> LENGTH: 20
<212> TYPE: PRT
<213> ORGANISM: Homo sapiens

<400> SEQUENCE: 27

```
Met Asp Glu Leu Tyr Pro Met Glu Pro Glu Glu Ala Asn Gly Ser
1               5                   10                  15

Glu Ile Leu Ala
            20
```

<210> SEQ ID NO 28
<211> LENGTH: 41
<212> TYPE: PRT
<213> ORGANISM: Homo sapiens

<400> SEQUENCE: 28

```
Asp Ala Glu Glu Asp Asp Ser Leu Ala Asn Ser Ser Asp Leu Leu Lys
1               5                   10                  15

Glu Leu Leu Glu Thr Gly Asp Asn Arg Glu Arg Ser His His Gln Asp
            20                  25                  30

Gly Ser Asp Asn Glu Glu Glu Val Ser
            35                  40
```

<210> SEQ ID NO 29
<211> LENGTH: 8
<212> TYPE: PRT
<213> ORGANISM: Homo sapiens

<400> SEQUENCE: 29

```
Tyr Gly Gly Phe Met Arg Gly Leu
1               5
```

<210> SEQ ID NO 30
<211> LENGTH: 12
<212> TYPE: PRT
<213> ORGANISM: Homo sapiens

<400> SEQUENCE: 30

Ser Pro Gln Leu Glu Asp Glu Ala Lys Glu Leu Gln
1               5                   10

<210> SEQ ID NO 31
<211> LENGTH: 22
<212> TYPE: PRT
<213> ORGANISM: Homo sapiens

<400> SEQUENCE: 31

Phe Ala Glu Ala Leu Pro Ser Asp Glu Glu Gly Glu Ser Tyr Ser Lys
1               5                   10                  15

Glu Val Pro Glu Met Glu
            20

<210> SEQ ID NO 32
<211> LENGTH: 29
<212> TYPE: PRT
<213> ORGANISM: Homo sapiens

<400> SEQUENCE: 32

Phe Ala Glu Ala Leu Pro Ser Asp Glu Glu Gly Glu Ser Tyr Ser Lys
1               5                   10                  15

Glu Val Pro Glu Met Glu Lys Arg Tyr Gly Gly Phe Met
            20                  25

<210> SEQ ID NO 33
<211> LENGTH: 7
<212> TYPE: PRT
<213> ORGANISM: Homo sapiens

<400> SEQUENCE: 33

Tyr Gly Gly Phe Met Arg Phe
1               5

<210> SEQ ID NO 34
<211> LENGTH: 20
<212> TYPE: PRT
<213> ORGANISM: Homo sapiens

<400> SEQUENCE: 34

Cys Asn Leu Asn Ser Pro Ala Glu Glu Thr Gly Glu Val His Glu Glu
1               5                   10                  15

Glu Leu Val Ala
            20

<210> SEQ ID NO 35
<211> LENGTH: 8
<212> TYPE: PRT
<213> ORGANISM: Homo sapiens

<400> SEQUENCE: 35

Leu Lys Glu Leu Leu Glu Thr Gly
1               5

<210> SEQ ID NO 36
<211> LENGTH: 8
<212> TYPE: PRT
<213> ORGANISM: Homo sapiens

<400> SEQUENCE: 36

Ser Asp Asn Glu Glu Glu Val Ser
1               5

```
<210> SEQ ID NO 37
<211> LENGTH: 11
<212> TYPE: PRT
<213> ORGANISM: Homo sapiens

<400> SEQUENCE: 37

Val Gly Arg Pro Glu Trp Trp Met Asp Tyr Gln
1               5                   10
```